(12) United States Patent
Shimoda et al.

(10) Patent No.: US 7,127,098 B2
(45) Date of Patent: Oct. 24, 2006

(54) IMAGE DETECTION METHOD AND ITS APPARATUS AND DEFECT DETECTION METHOD AND ITS APPARATUS

(75) Inventors: Atsushi Shimoda, Hiratsuka (JP); Masahiro Watanabe, Yokohama (JP); Syunji Maeda, Yokohama (JP); Hiroshi Goto, Ushiku (JP); Tadashi Suzuki, Kasama (JP)

(73) Assignee: Hitachi, Ltd., Tokyo (JP)

( * ) Notice: Subject to any disclaimer, the term of this patent is extended or adjusted under 35 U.S.C. 154(b) by 698 days.

(21) Appl. No.: 10/242,362

(22) Filed: Sep. 13, 2002

(65) Prior Publication Data

US 2003/0053676 A1 Mar. 20, 2003

(30) Foreign Application Priority Data

Sep. 13, 2001 (JP) .............................. 2001-278789

(51) Int. Cl.
*G06K 9/00* (2006.01)
*H01L 27/00* (2006.01)
*G01J 1/42* (2006.01)
*G01B 11/30* (2006.01)

(52) U.S. Cl. ................ 382/145; 250/208.3; 250/208.1; 356/603; 356/608

(58) Field of Classification Search ................ 382/145; 356/602–609; 250/208.1
See application file for complete search history.

(56) References Cited

U.S. PATENT DOCUMENTS

| 4,707,610 | A | * | 11/1987 | Lindow et al. | ........ 250/559.22 |
| 5,151,609 | A | * | 9/1992 | Nakagawa et al. | .... 250/559.22 |
| 5,266,790 | A | * | 11/1993 | Markle et al. | ........... 250/201.2 |
| 5,305,092 | A | * | 4/1994 | Mimura et al. | ............. 356/609 |
| 5,780,866 | A | * | 7/1998 | Yamamura et al. | .... 250/559.22 |
| 5,985,497 | A | * | 11/1999 | Phan et al. | .................... 430/30 |
| 6,091,075 | A | * | 7/2000 | Shibata et al. | ......... 250/559.44 |
| 6,107,637 | A | * | 8/2000 | Watanabe et al. | ........ 250/559.3 |
| 6,124,950 | A | * | 9/2000 | Honda | ........................ 358/474 |
| 6,330,066 | B1 | * | 12/2001 | Tanaka et al. | ............... 356/609 |
| 6,483,580 | B1 | * | 11/2002 | Xu et al. | ..................... 356/300 |
| 6,603,877 | B1 | * | 8/2003 | Bishop | ........................ 382/165 |
| 6,826,298 | B1 | * | 11/2004 | O'Dell et al. | ............... 382/149 |
| 2003/0170552 | A1 | * | 9/2003 | Miyashita et al. | ............ 430/30 |

FOREIGN PATENT DOCUMENTS

| JP | 04-076450 | 3/1992 |
| JP | 09-036036 | 2/1997 |

* cited by examiner

*Primary Examiner*—Bhavesh M. Mehta
*Assistant Examiner*—Utpal Shah
(74) *Attorney, Agent, or Firm*—Antonelli, Terry, Stout and Kraus, LLP.

(57) ABSTRACT

The present invention provides an image detection system capable of picking up a high resolution image of the surface condition of a circuit pattern-formed wafer without being affected by steep pattern steps, discontinuous reflectance distributions and optically transparent substances which are formed after resist patterns are formed and removed. A defect detection apparatus using such an image detection apparatus is also provided by the invention. The present invention is implemented by a configuration comprising a scanning stage having a sample mounted thereon, an image pickup system for picking up a surface image of the sample, height detection means for detecting the surface height of the sample at plural points including two points which are respectively on the opposite sides of the image pickup position in the scanning direction, sample height calculation means for calculating the height of the sample at the image pickup position by using the detected heights and focusing means for focusing the image pickup system by using the calculated sample height.

28 Claims, 35 Drawing Sheets

FIG. 1
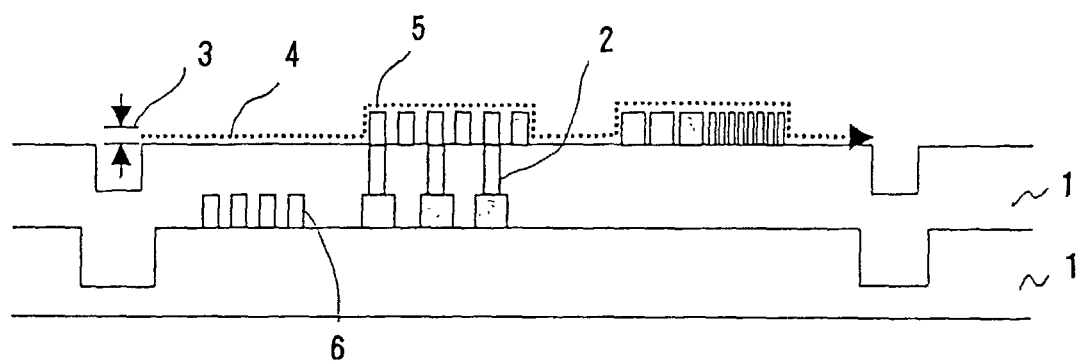
(a)
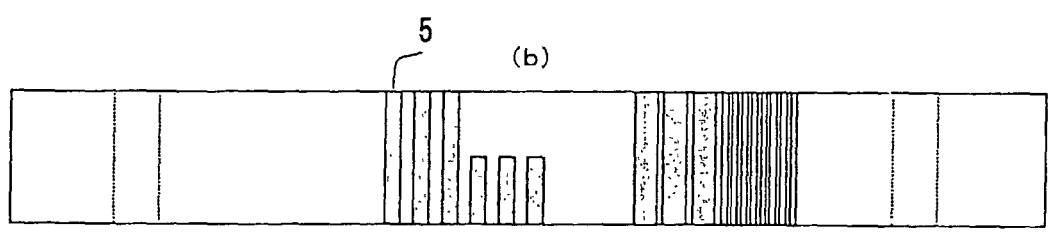
(b)
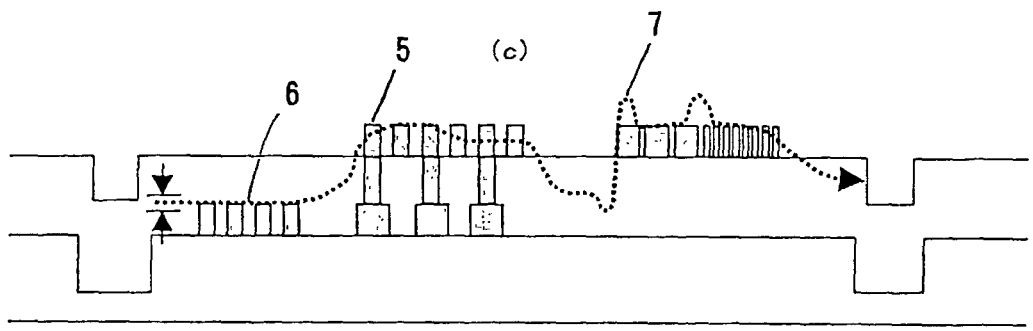
(c)
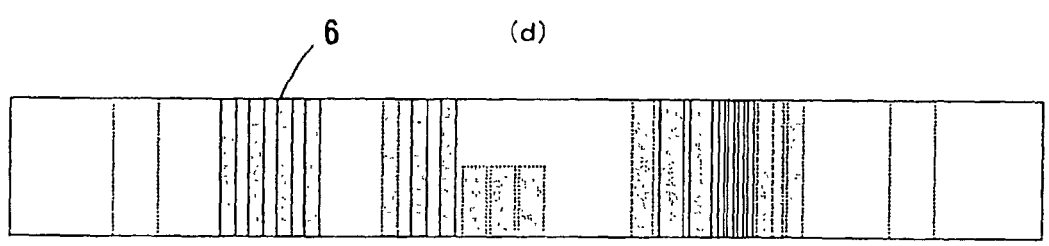
(d)

FIG. 7
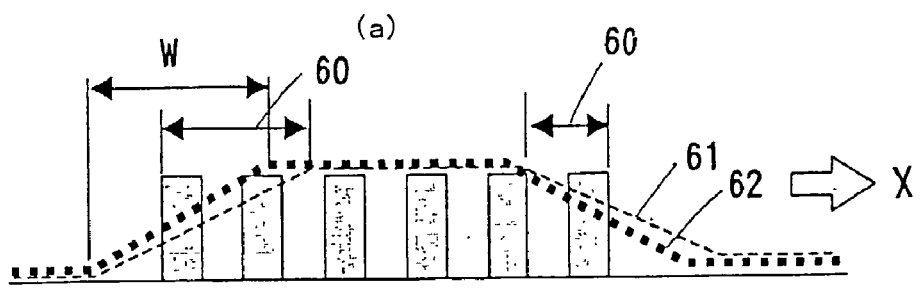
(a)
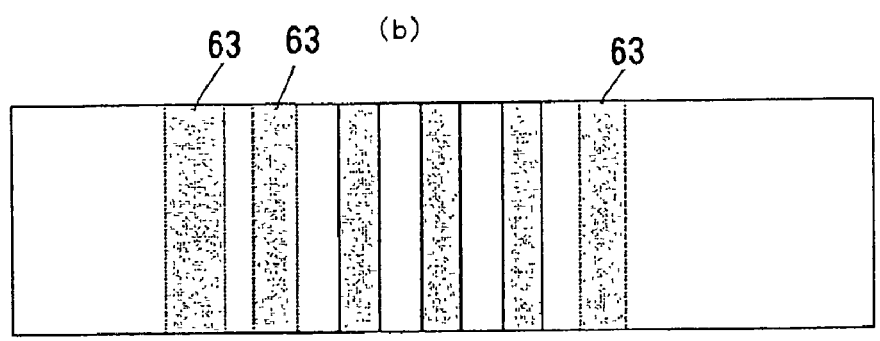
(b)
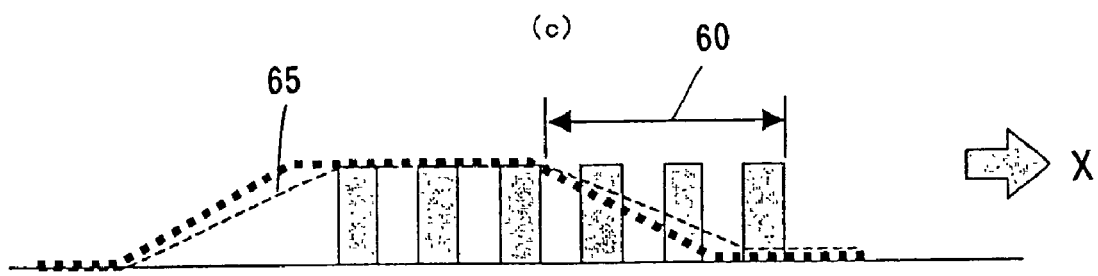
(c)
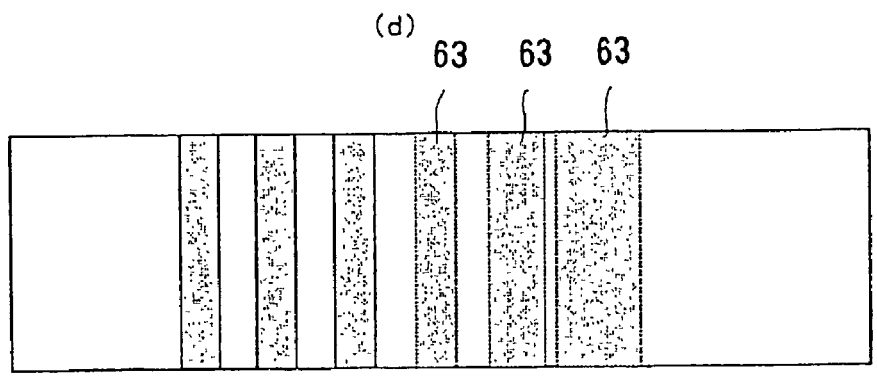
(d)

FIG. 11
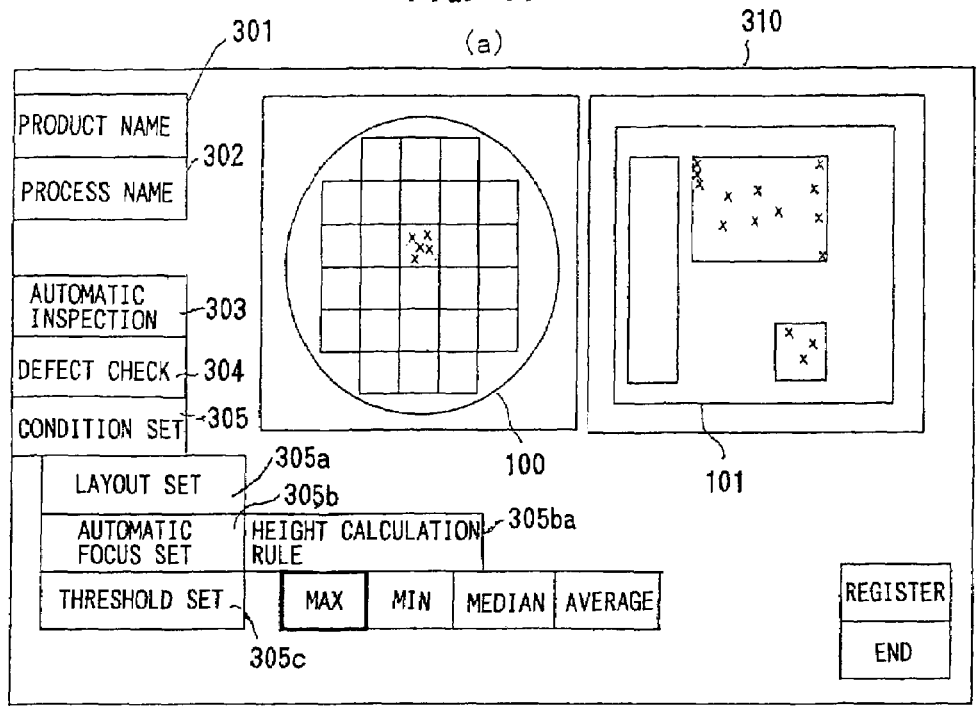
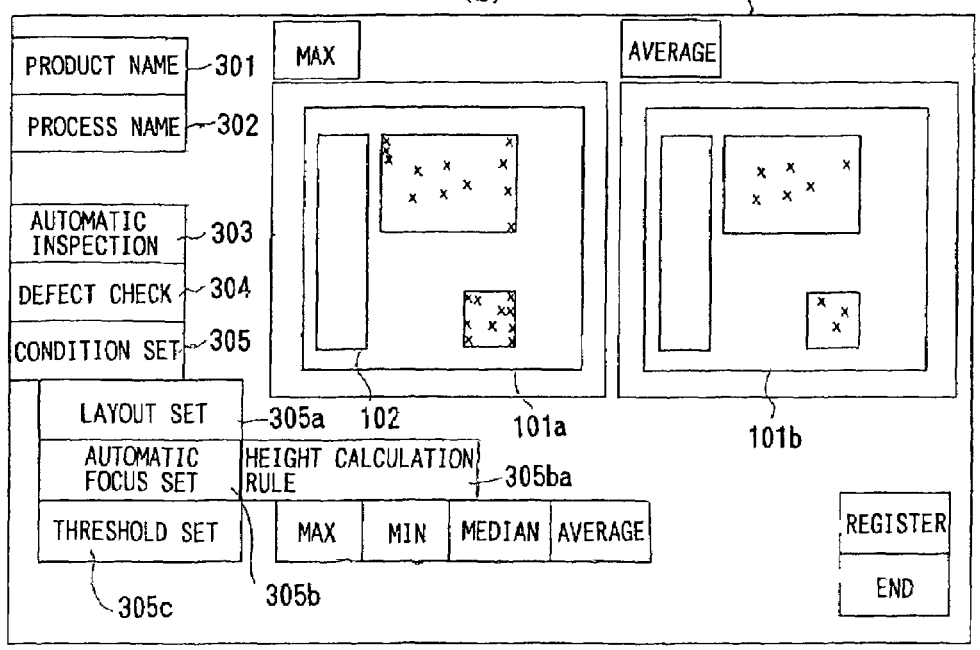

FIG. 12
(a)
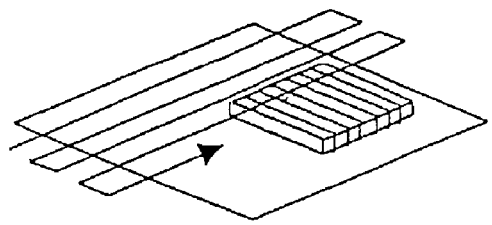
(b)
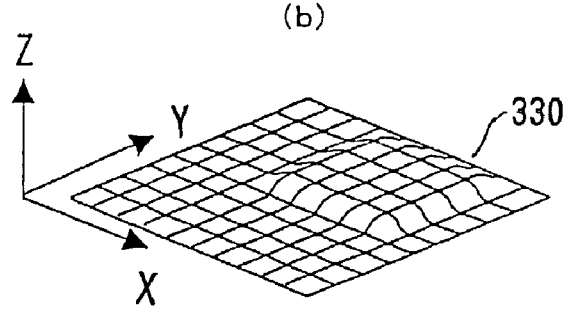
(c)
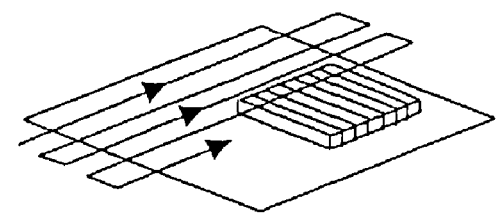
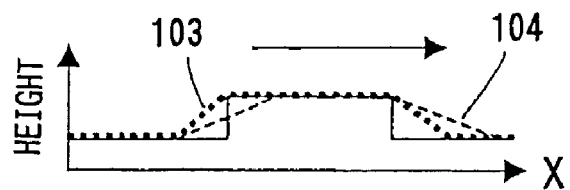
(d)
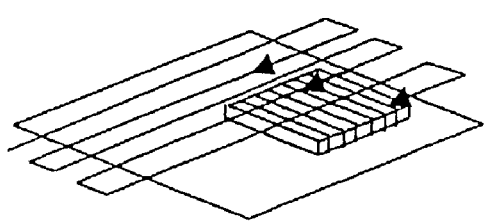
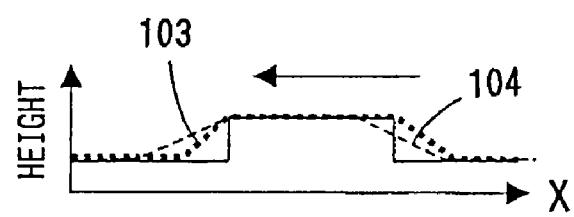
(e)
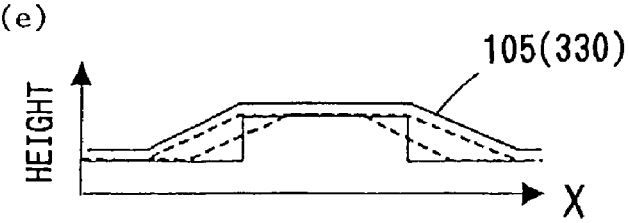

FIG. 14
(a)
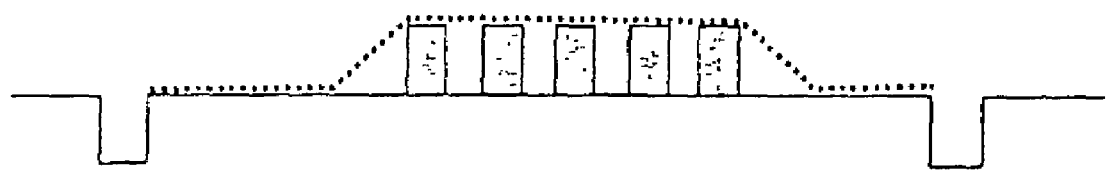
(b)
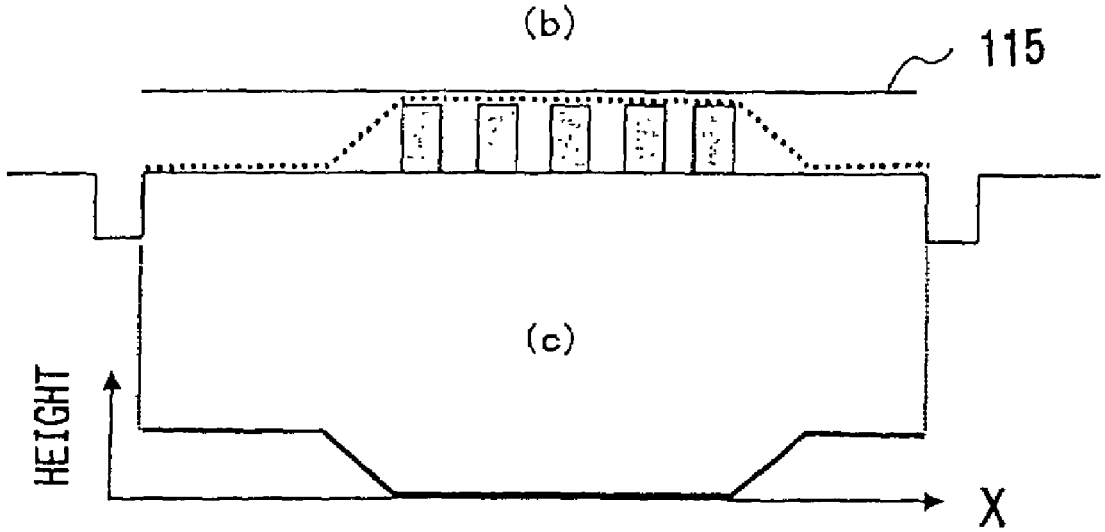
115
(c)
HEIGHT
X
(d)
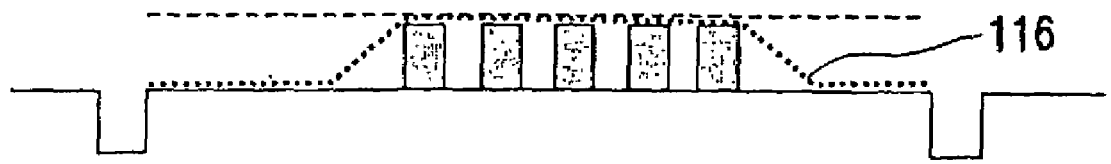
116

FIG. 21
(a)
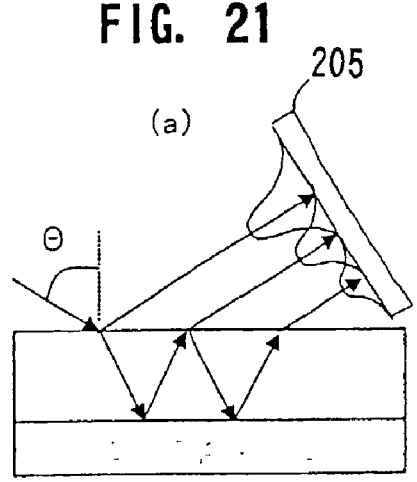
(b)
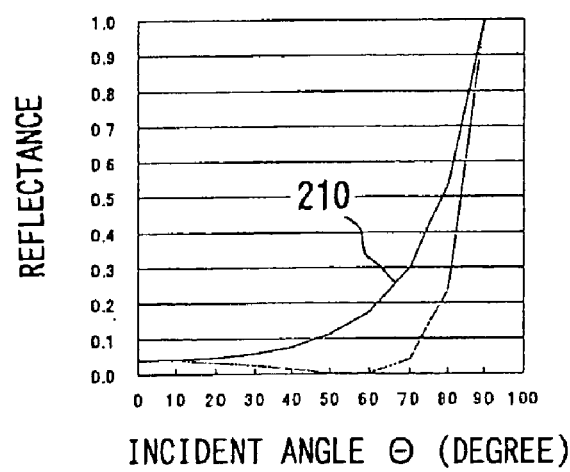
(c)
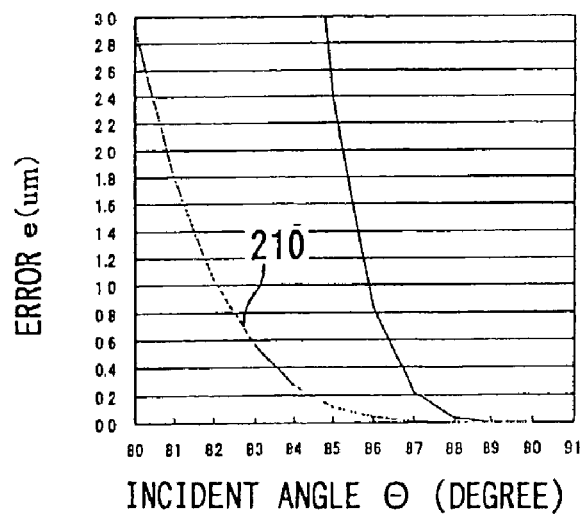

FIG. 23
(a)
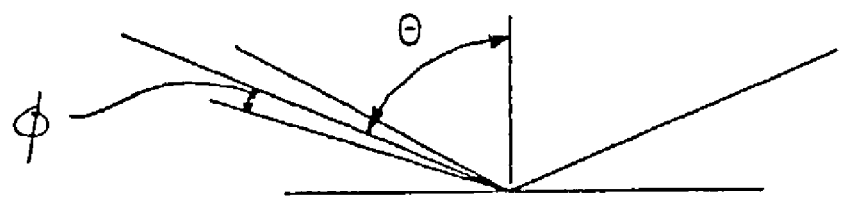
(b)
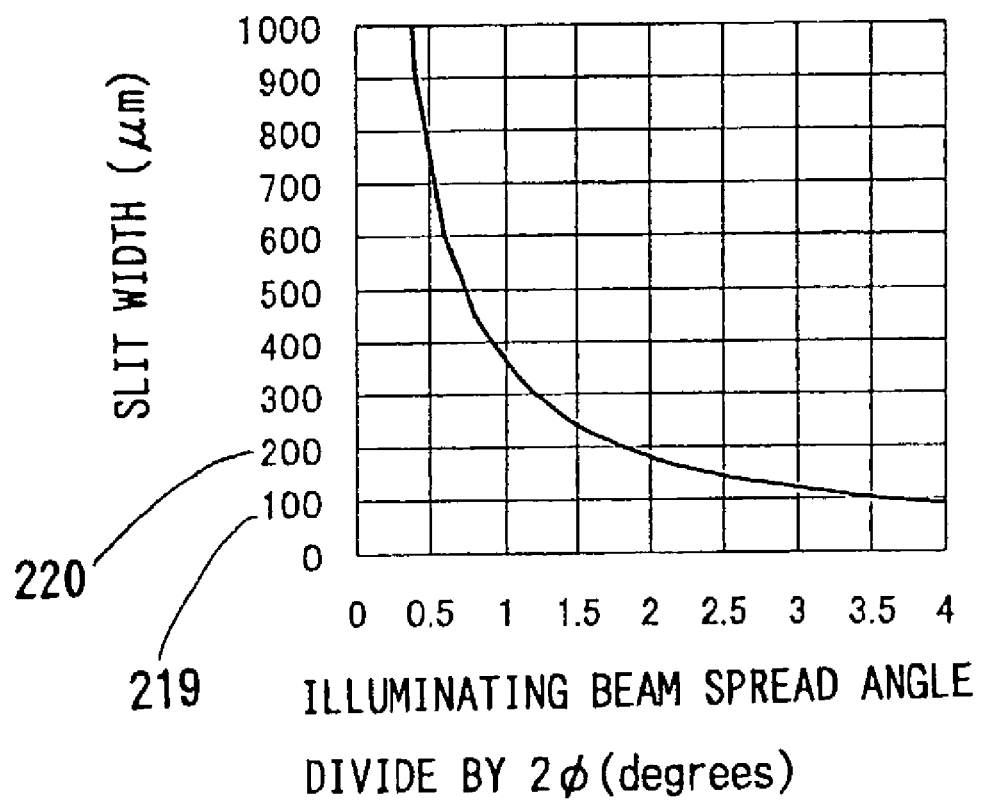

FIG. 24
(a)
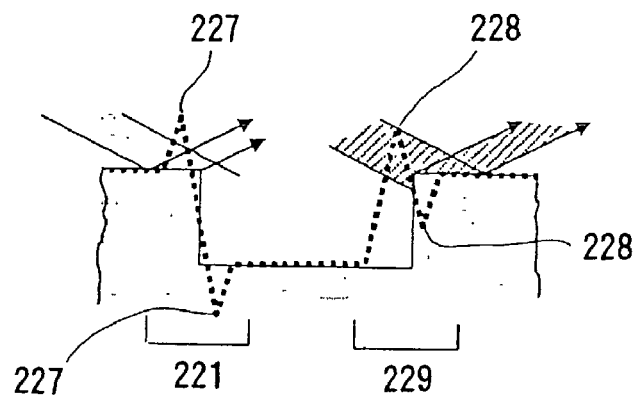
(b)
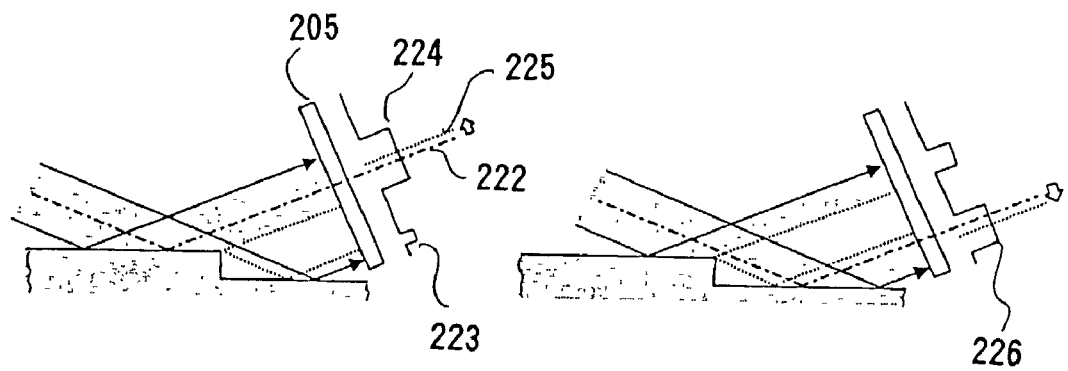
(c)
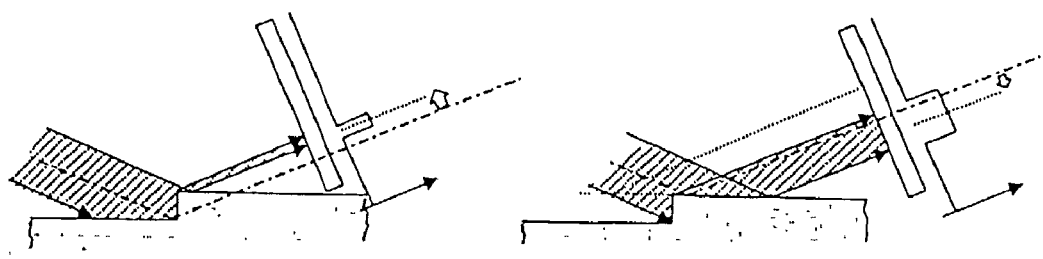

FIG. 29
(a)
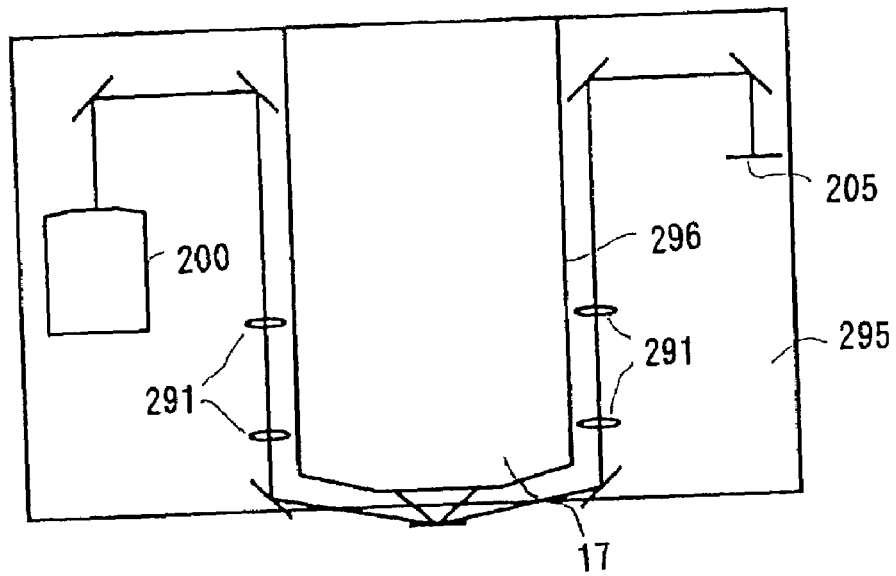
(b)
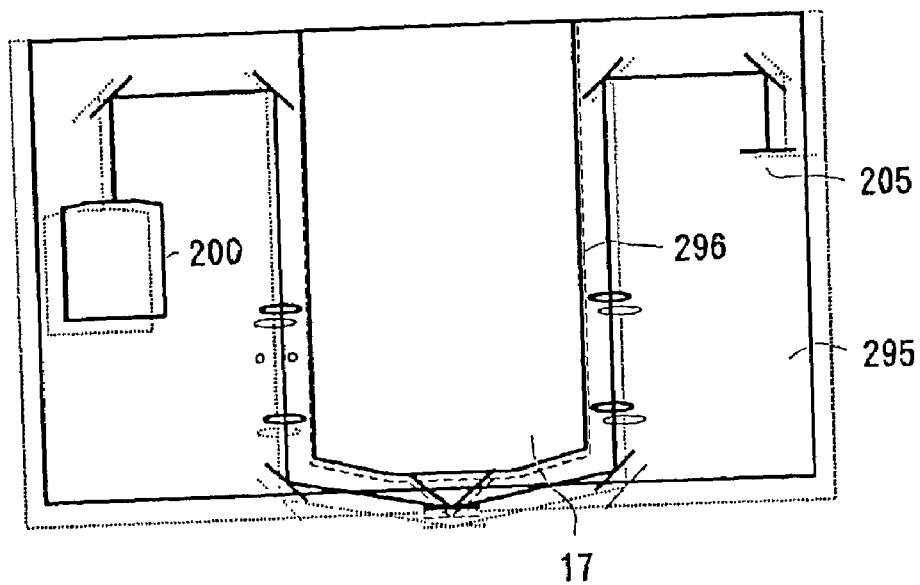
(c)
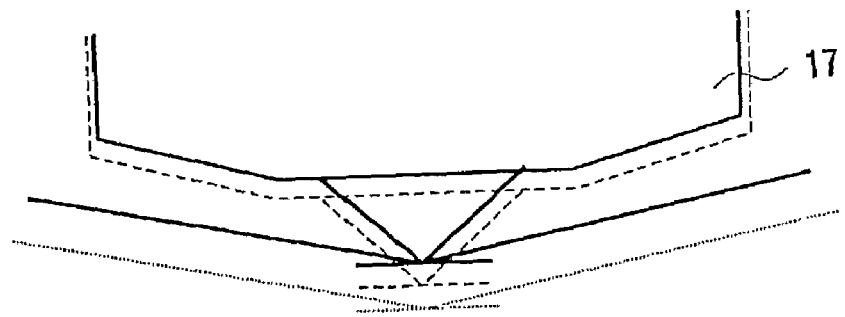

FIG. 30
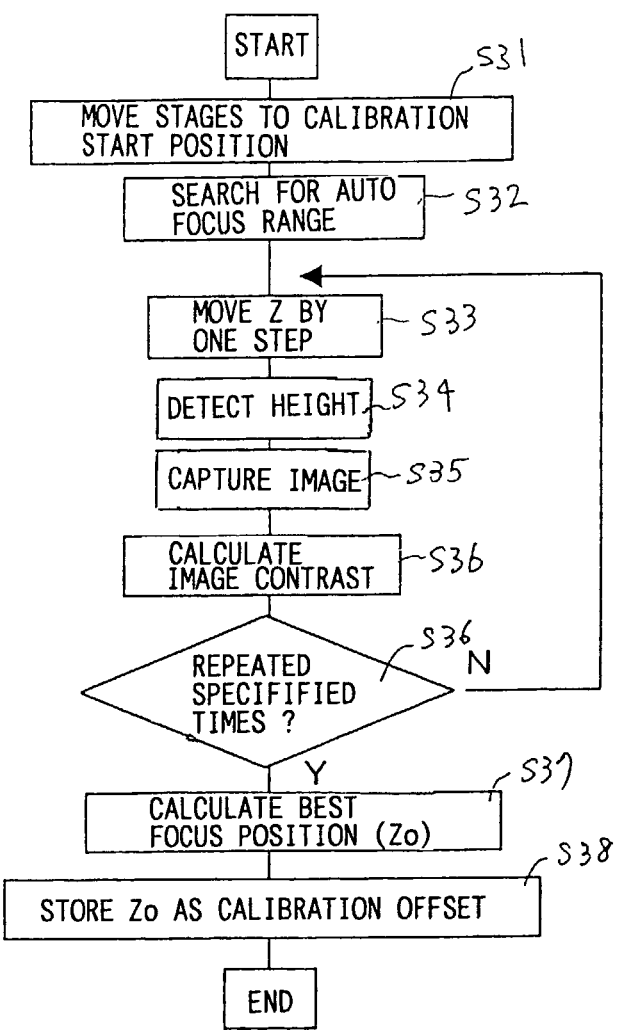
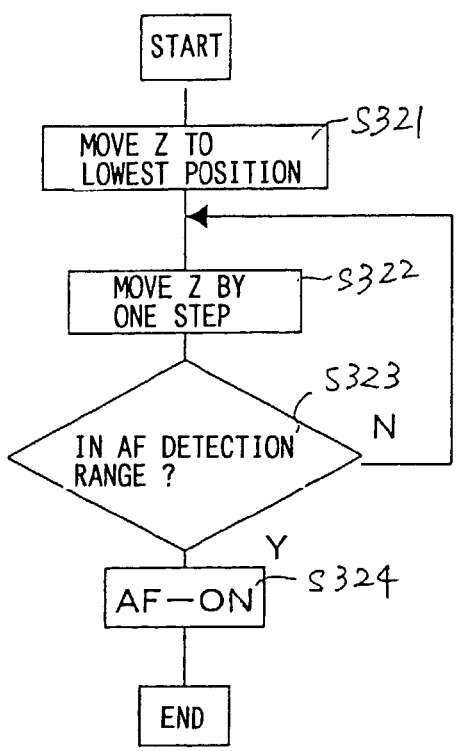
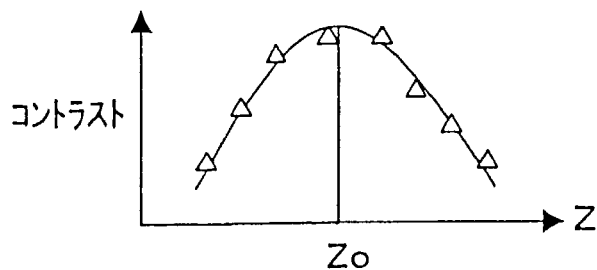

FIG. 32
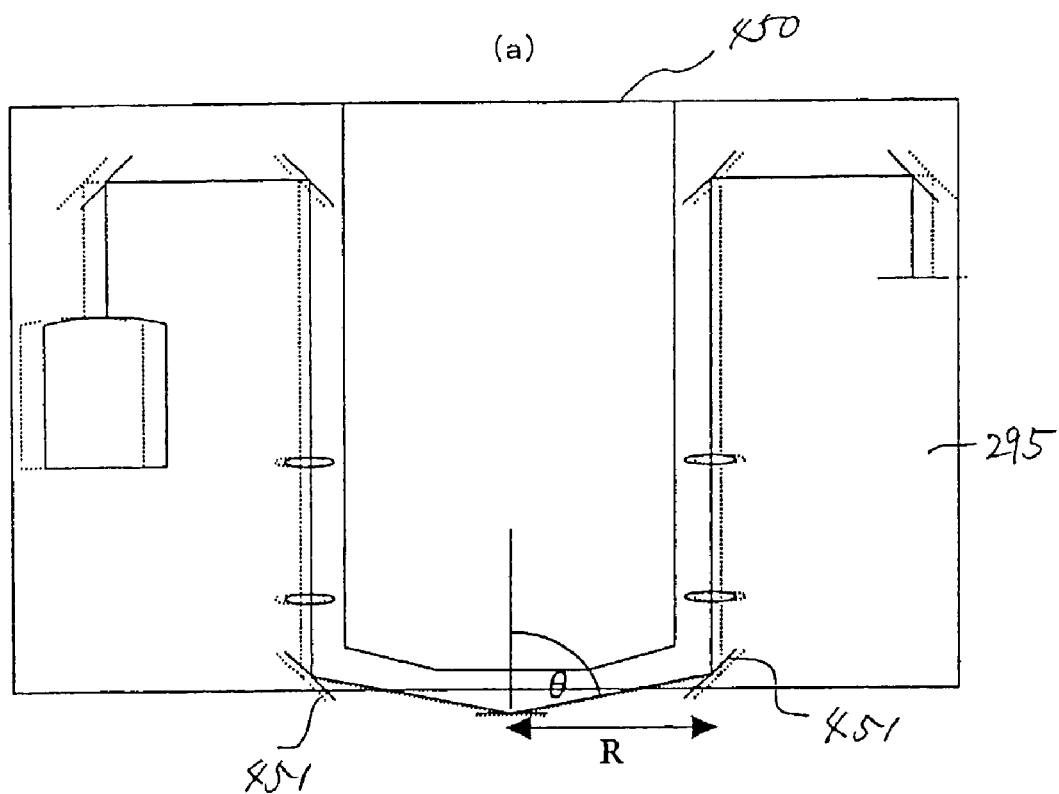
(a)
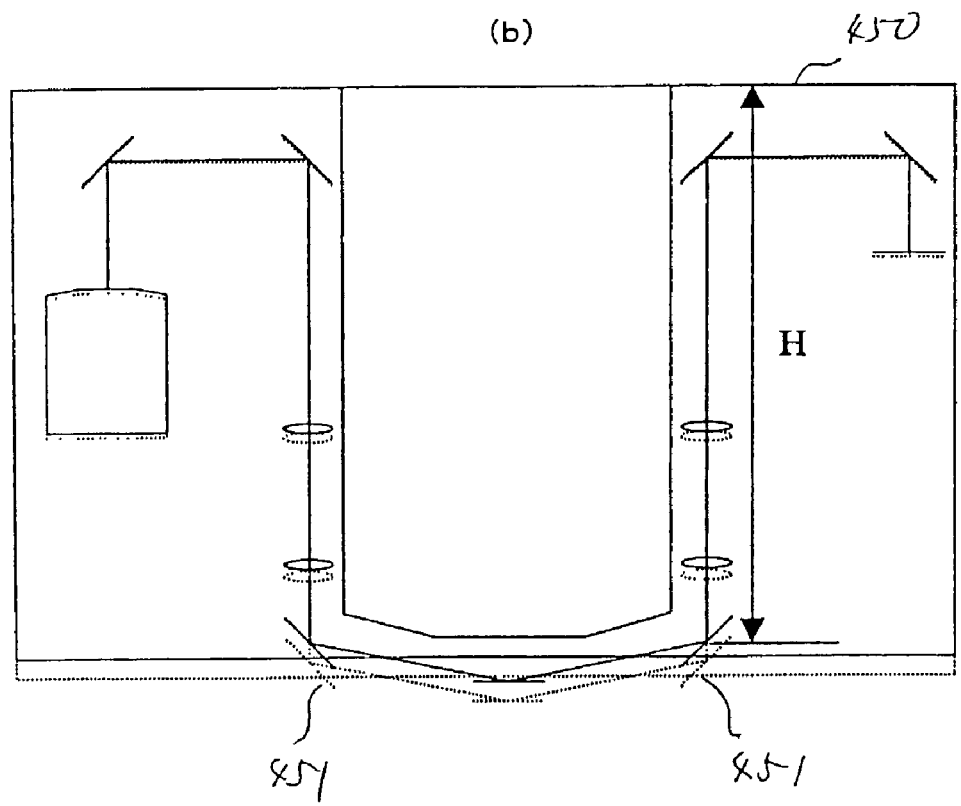
(b)

FIG. 35
(a)
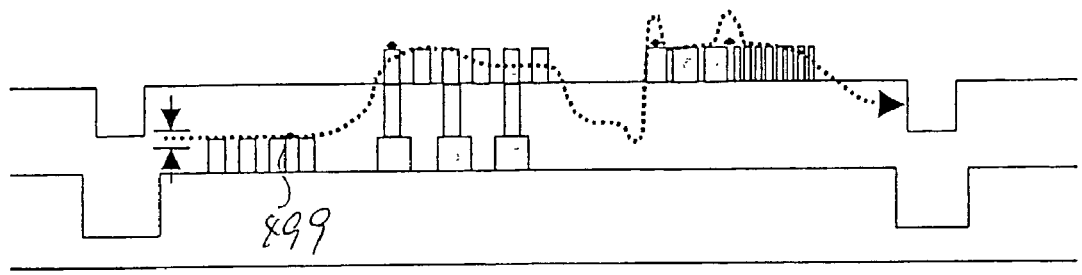
(b)
(c)
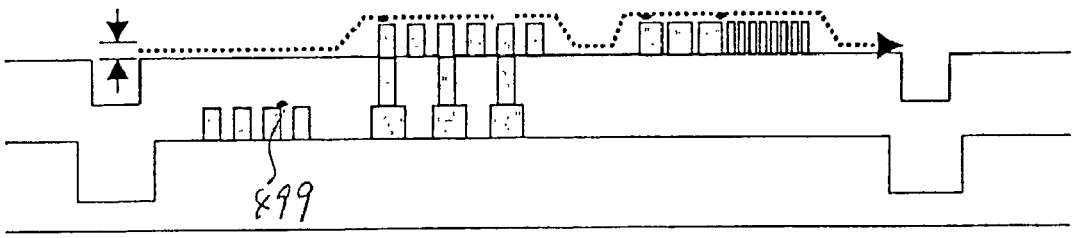
(d)
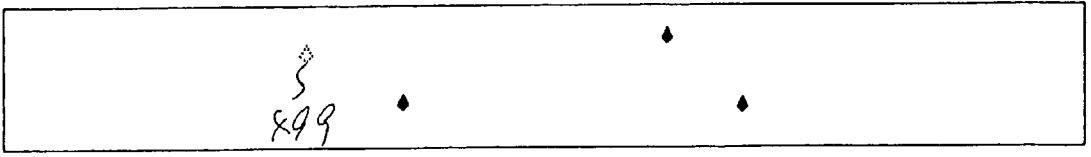

FIG. 36
(a)
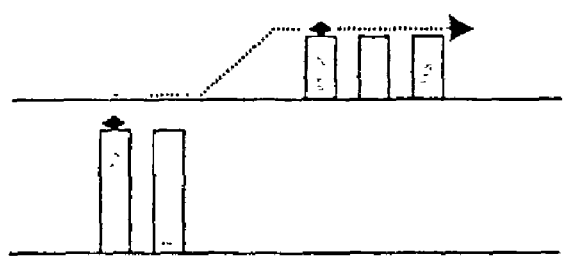
(b)
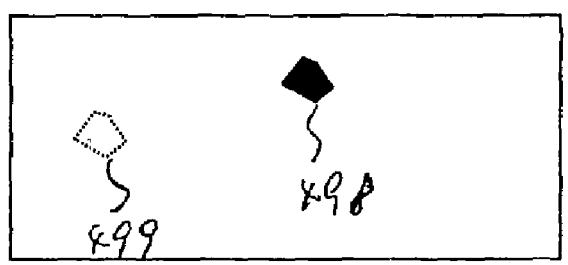
(c)
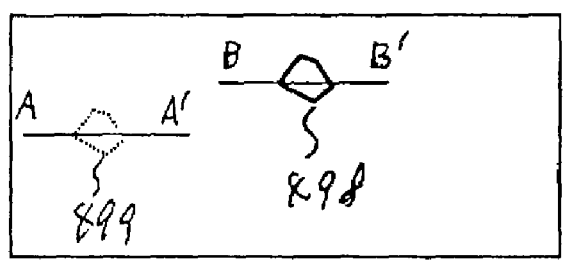
(d)
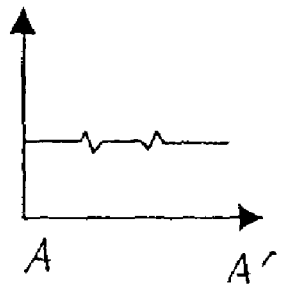
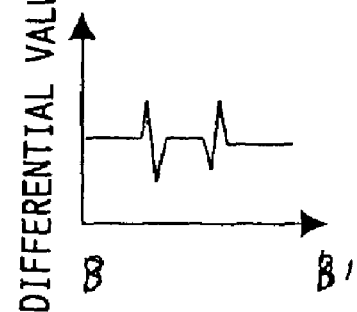

FIG. 37
(a)
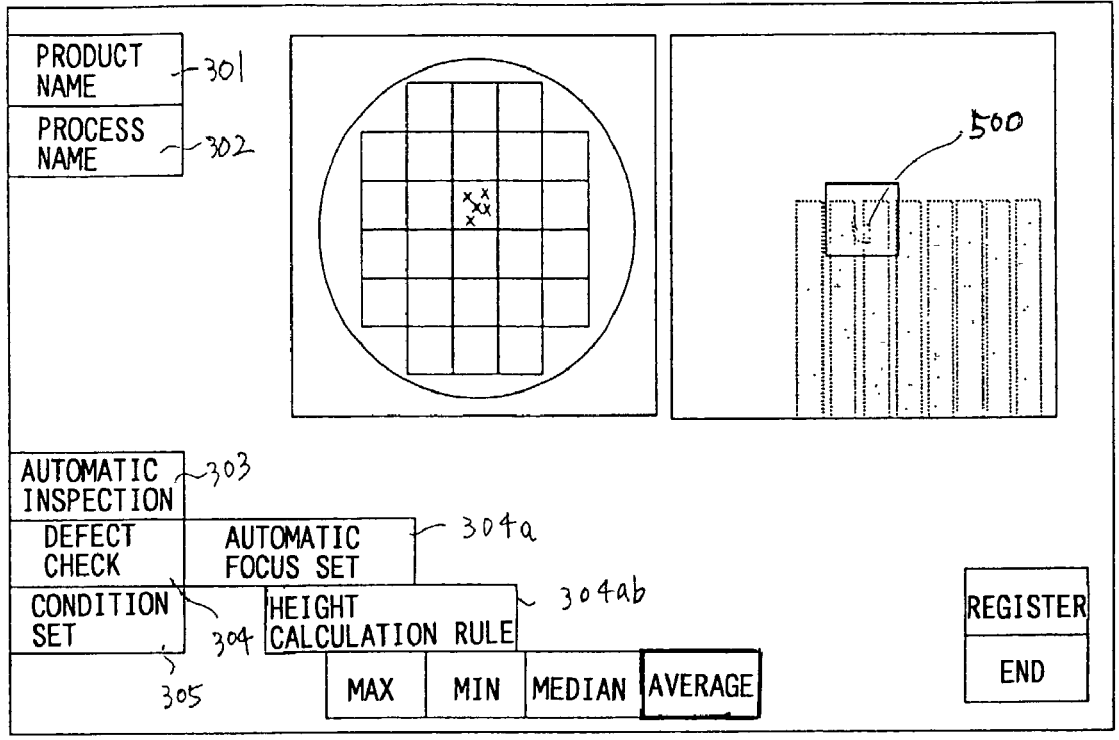
(b)
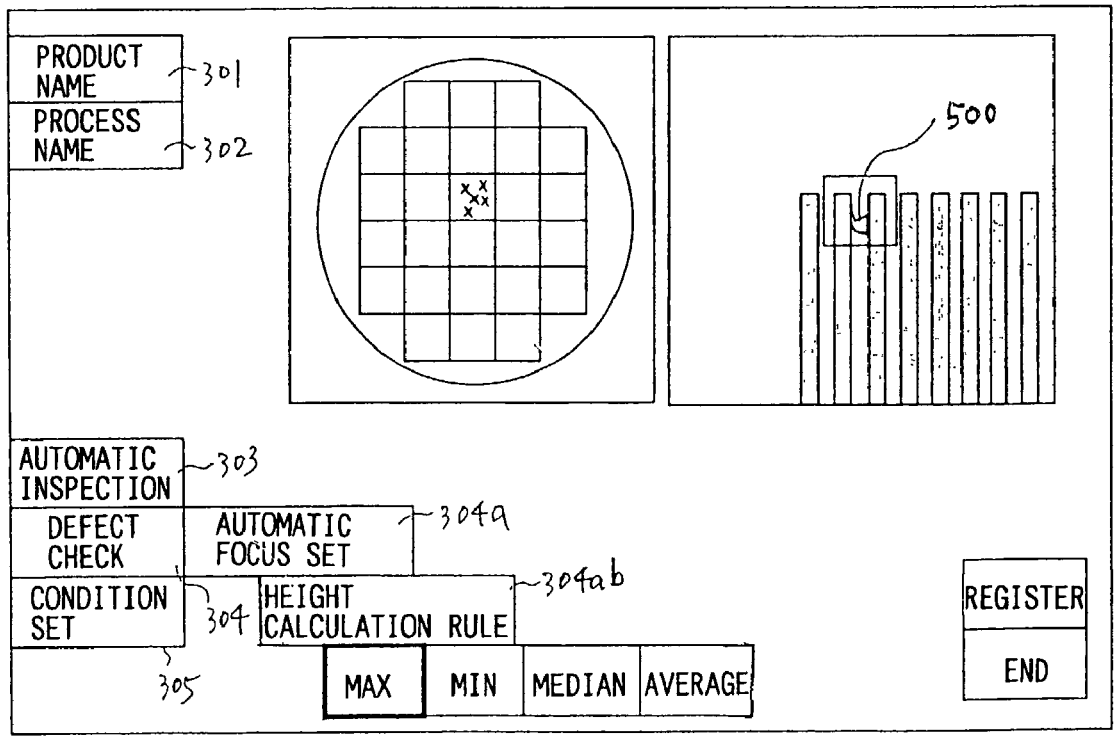

IMAGE DETECTION METHOD AND ITS APPARATUS AND DEFECT DETECTION METHOD AND ITS APPARATUS

BACKGROUND OF THE INVENTION

The present invention relates to an image detection apparatus which captures a high resolution surface image of a sample made of various materials and having an uneven surface, such as a semiconductor wafer on which fine circuit patterns are formed, and a defect detection/measurement apparatus using that image. In particular, this invention is preferably applicable to an apparatus which employs a high resolution and narrow focal depth optical system such as an optical microscope using a DUV light source.

As systems for picking up a high resolution surface image of a sample made of various materials and having an uneven surface, there are pattern defect detection apparatuses for semiconductor wafers.

In Japanese Patent Laid-Open No. 4-76450, a focus detection method is disclosed for semiconductor wafer pattern defect detection apparatuses. In this conventional method, a reticle inserted in an illuminating light path is projected onto the sample via an objective lens and an image of the reticle pattern reflected from the sample is shaded by another reticle placed in the detection light path. The height of the sample is detected by the increase or decrease in the quantity of light which has passed the reticle.

Similar to pattern defect detection apparatuses, projection exposure apparatuses also have a high resolution optical system which must be focused on the surface of a sample made of various materials and having an uneven surface. For automatic focusing in a projection exposure apparatus, a height detection method is disclosed in Japanese Patent Laid-Open No. 9-36036. Wafers to be processed by a projection exposure apparatus is coated entirely with a resist, an optically transparent-substance. To accurately detect the surface height of the resist in this disclosed method, S-polarized light is irradiated to the wafer at an incident angle of 85 degrees or more so that reflection at the transparent surface layer is raised.

The first conventional technique mentioned above is immune to the unevenness of the surface of the sample and the distribution of reflection over the surface of the sample. However, it has a drawback that the detected height does not necessarily agrees with that of the surface layer since where the surface layer is an optically transparent substance, irradiated light penetrates through the surface layer and is reflected by an under layer.

The second conventional technique mentioned above provides high accuracy height detection if the whole surface of the wafer is smoothly coated with a resist. However, sufficient care is not given to steep dents and bumps which may occur to the circuit pattern on the wafer after a resist pattern is formed or removed.

SUMMARY OF THE INVENTION

In view of the prior art mentioned above, the present invention has been made, and there is provided an image detection method/apparatus capable of picking up a high resolution image of the surface condition of a circuit pattern-formed wafer without being affected by steep pattern steps, discontinuous reflectance distributions and optically transparent substances which are formed after resist patterns are formed and removed, and an defect detection method/apparatus using this image detection method/apparatus.

The present invention also provides an image detection method/apparatus capable of picking up a clear image of a specific pattern of concern by keeping the sample surface to a preset height, and an defect detection method/apparatus using this image detection method/apparatus.

In addition, the present invention provides a defect detection method for a sample having a plurality of layer patterns, comprising the steps of: picking up a surface image of the sample by using image pickup means while moving a scanning stage having the sample mounted thereon; comparing the picked up image with a standard reference image to detect defect candidates; picking out a real defect from the detected defect candidates; extracting a feature amount from the real defect picked out; and outputting the extracted feature amount information about the real defect, wherein when a surface image of the sample is picked up, the focus of the image pickup means is adjusted in such a manner that the uppermost layer pattern of the sample mounted on the scanning stage is in focus and the lower layer patterns are out of focus.

Further, the present invention provides a defect detection method for a sample having a plurality of layer patterns, comprising the steps of: picking up a surface image of the sample in such a manner that the uppermost layer pattern of the sample mounted on the scanning stage is in focus and the lower layer patterns are out of focus; comparing the picked up image with a reference image to detect defect candidates; and picking out a real defect in the uppermost layer pattern from the detected defect candidates, and a defect detection apparatus using this defect detection method.

Further, the present invention provides focusing means characterized in that it uses different functions for controlling the focus upward and downward respectively with respect to the sample surface, in particular, the upward control function has a higher gain coefficient than the lower control function in order to achieve appropriate image detecting condition.

These and other objects, features and advantages of the invention will be apparent from the following more particular description of preferred embodiments of the invention, as illustrated in the accompanying drawings.

BRIEF DESCRIPTION OF THE DRAWINGS

FIG. 1(a) is a sectional view of a semiconductor wafer, FIG. 1(b) illustrate an image of the uppermost layer pattern, FIG. 1(c) is a sectional view of a semiconductor wafer and FIG. 1(d) is a diagram for explaining errors induced when wafer heights are detected by optical means;

FIGS. 7(a) through 7(d) are diagrams for explaining how defocus occurs at step boundaries;

FIGS. 11(a) and 11(b) show examples of focusing condition setting screens;

FIG. 12(a) is a diagram for explaining how patterns are scanned when a focus map is prepared, FIG. 12(b) is a bird's-eye view of the focus map, FIG. 12(c) shows how the height detection signal changes at step boundaries in rightward scan, FIG. 12(d) shows how the height detection signal changes at step boundaries in leftward scan and FIG. 12(e) is a result of combining data obtained by rightward scan and data obtained by leftward scan;

FIGS. 14(a) through 14(d) are diagrams for explaining a fourth focusing method according to the present invention;

FIG. 17(a) shows the locus of focal points, FIG. 17(b) shows the height detecting operation timing signal, FIG. 17(c) is a detected image and FIG. 17(d) is an image of difference between the left chip image and right chip image. On the other hand, FIG. 17(e) is the locus of focal points, FIG. 17(f) shows the chip start signal asserted according to the position of the X stage, FIG. 17(g) shows the height detecting operation timing signal, FIG. 17(h) is a detected image and FIG. 17(i) is an image of difference between the left chip image and the right chip image;

FIG. 18(c) is a sectional view of a wafer showing the locus of heights detected when the wafer is scanned left to right, corresponding to 127 of FIG. 18(b), FIG. 18(d) shows an image detected when scanned as FIG. 18(c), FIG. 18(e) shows the locus of heights detected when the wafer is scanned right to left, FIG. 18(f) is an image detected when scanned as FIG. 18(e) and FIG. 18(g) is an image of difference between FIGS. 18(d) and 18(f). FIG. 18(h) is a sectional view of a wafer showing the locus of focal points when the wafer is scanned left to right, corresponding to numeral 130 of FIG. 18(b). FIG. 18(i) is an image obtained when the focus is controlled as FIG. 18(h). FIG. 18(j) is a sectional view of a wafer showing the locus of focal points when the wafer is scanned right to lest, corresponding to numeral 129 of FIG. 18(b). FIG. 18(k) is an image of difference between FIGS. 18(i) and 18(k);

FIG. 21(a) is a sectional view of a sample where a slanting light beam is reflected at the top and bottom surfaces of a transparent film, FIG. 21(b) shows the dependence of the incident beam's reflectance upon the incident angle and FIG. 21(c) shows the relation between the incident angle of the incident beam and the height detection error;

FIG. 23(a) shows the condition of the illuminating light irradiated to the sample and FIG. 23(b) shows the relation between the slit width and the illuminating beam's spread angle divided by 2 ($\phi$);

FIGS. 24(a) through (c) show a case where step boundaries are illuminated by an illuminating beam in the configuration of FIG. 20;

FIGS. 29(a) through (c) are diagrams for explaining the drift of the origin of the height detection optical system of FIG. 20 which is integrated into the defect detection apparatus shown in FIG. 2;

FIGS. 30(a) and (b) are a flowchart showing the calibration procedure and FIG. 30(c) shows the relation between the sample height and the contrast.

FIGS. 32(a) and (b) are diagrams for explaining the amount of drift of the height detection optical system;

FIG. 35(a) is a sectional view of a wafer indicating the locus of focal points controlled by a conventional method, FIG. 35(b) is a defect detection result obtained by scanning the wafer as FIG. 35(a), FIG. 35(c) is a sectional view of a wafer indicating the locus of focal points controlled by a method of the present invention and FIG. 35(d) is a defect detection result obtained by scanning the wafer as FIG. 35(c);

FIG. 36(a) shows a sectional view of a wafer where the uppermost pattern layer is formed after a transparent film is formed to cover the lower layer patterns, FIG. 36(b) is an image obtained by picking up the pattern of FIG. 36(a) and FIG. 36(c) is a differential image obtained by differentiating the image of FIG. 36(b) and FIG. 36(d) is sectional views of the differential image of FIG. 36(c).

FIGS. 37(a) and 37(b) are an example implementation of a review screen according to the present invention.

DESCRIPTION OF THE PREFERRED EMBODIMENTS

Figure 2:
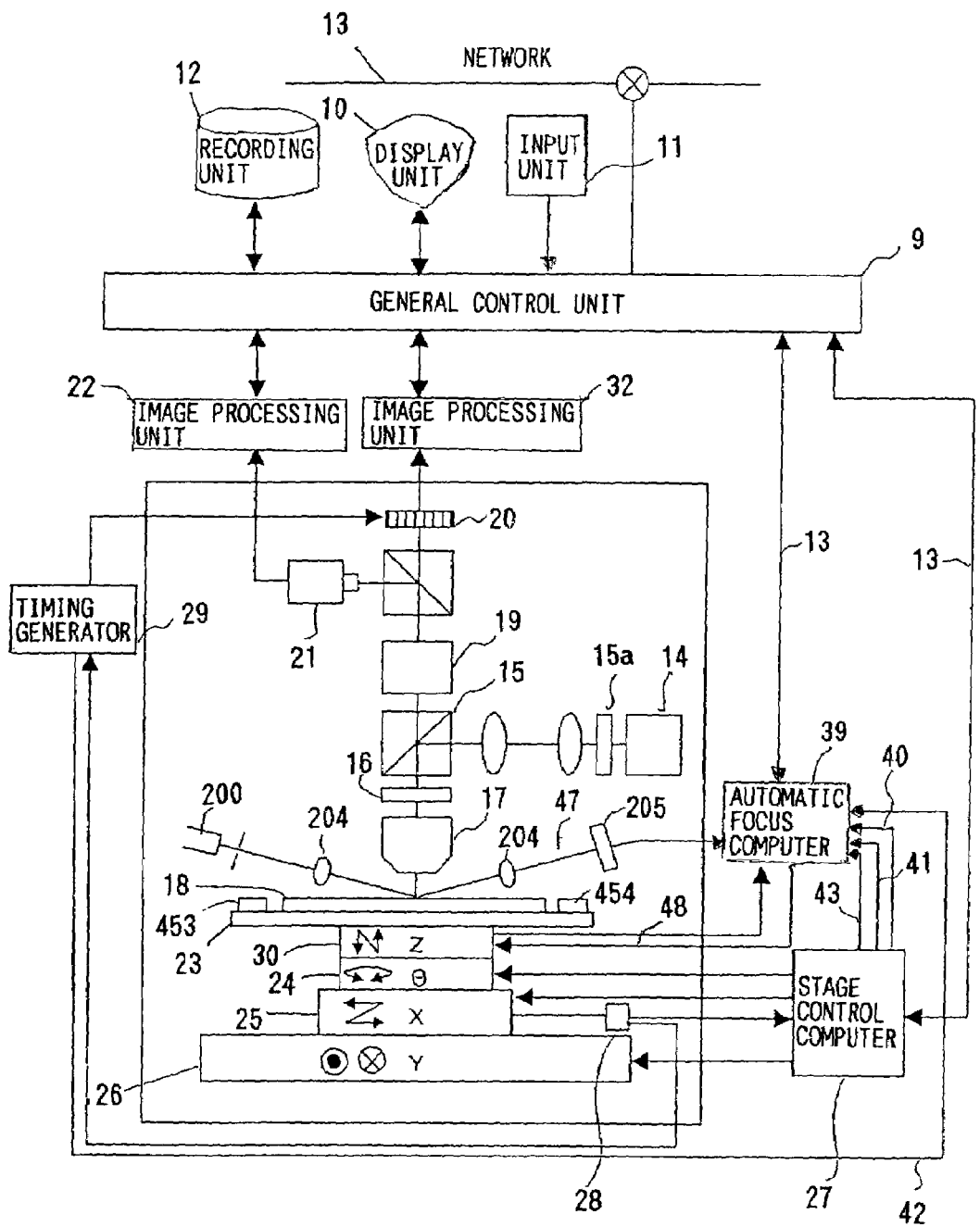
FIG. 2 is a schematic diagram showing a general configuration of a semiconductor wafer defect detection apparatus according to a first embodiment of the present invention.

Embodiments of the present invention will thereinafter be described with reference to the drawings.

Described below are embodiments of optical inspection systems according to the present invention to inspect/measure fine circuit patterns formed on a semiconductor wafer, an object to be inspected. Defect inspection of a fine circuit pattern formed on a semiconductor wafer or the like is done by comparing the pattern with a reference pattern or a pattern of the same kind on the wafer. In this comparison inspection method, however, reliability of the inspection result is much affected by the quality of the obtained image since the image must be compared with a similar image. Image quality may be deteriorated by various factors and the largest factor is defocus. To pick up a high-resolution image of a fine circuit pattern without defocus, it is necessary to accurately detect the surface height of the sample and keep the focus aligned to the surface.

FIG. 1 explains how height errors are induced when the height of a wafer is detected by optical means. FIG. 1(a) is a cross sectional view of the semiconductor wafer. The semiconductor wafer has multiple circuit pattern layers stacked and insulated with each other by optically transparent inter-layer films 1. Circuit patterns on the respective layers are connected with each other through contact holes 2. Used to find what problem remains to be solved in each manufacture process is an optical inspection system. Immediately after a process is completed, the optical inspection system is used to pick up an image of a fine circuit pattern for detecting defects, such as short and open, in the circuit pattern. To sensitively detect micro-defects, the sample surface must be aligned to within the focal depth 3 so that a clear pattern image can be obtained. A broken line 4 is drawn along the center of the focal depth when the wafer surface is positioned ideally. As the result, a clear image of the uppermost layer circuit pattern 5 is obtained as shown in FIG. 5(b). Note that the lower most layer pattern 6 is defocused and its image is not picked up. For inspection of a semiconductor wafer having multiple layers, it is necessary to identify which manufacture process involves a problem and must be improved. For this purpose, after a circuit pattern is formed, it is preferable to detect only the defects in the uppermost layer by defocusing the lower layer patterns so that the inspection result is not affected by defects in the lower layers.

However, conventional optical means cannot always detect the height of the wafer surface steadily as shown in FIG. 1(c). This may result in a deteriorated image quality (due to defocus) as shown in FIG. 1(d) and cause overlooked defects and falsely detected defects. When optical means is used to detect the surface of a semiconductor wafer, the following errors must be considered.

[Error Induced by Transparent Film]

The illuminating beam used for height detection penetrates an inter-layer film and is reflected by a lower layer. Therefore, the detected height is not stable because it is subject to the material and shape of the lower layer. For example, this may cause confusion between the uppermost layer and the lower layer, resulting in the beam focused to the lower layer instead of the uppermost layer whose image must be picked up.

[Error Induced at Step Boundary]

Where a step exists, the height of the step boundary is obtained by averaging the height of the upper surface and the height of the lower surface. As a result, both upper and lower surfaces are defocused around the boundary. In addition, it is possible that an unreal height may be detected as indicated by reference numeral 7. Also in this case, the detected imaged is defocused.

[Error Induced by Discontinuous Reflectance]

Where reflectance changes discontinuously, it is possible that an unreal height may be detected, resulting in a detected image defocused.

It is an object of the present invention to steadily detect the surface height of a sample made of various materials and having a uneven surface, such as a semiconductor wafer, and steadily detect a high resolution image of the surface of the sample by controlling the image pickup condition based on the detected surface height.

FIG. 2 shows a semiconductor wafer defect detection apparatus according to a first embodiment of the present invention. As an embodiment in its particularly preferable application field, an optical pattern defect detection apparatus using an optical microscope with a DUV light source is described.

[General Control Unit]

A general control unit 9 governs the general operation of the apparatus. The general control unit 9 is provided with a display unit 10 for displaying inspection information, etc. In addition, the general control unit 9 is provided with an input unit 11 for taking in user information. Further, the general control unit 9 is connected to a recording unit 12 for managing inspection data and recipe data. Further, the general control unit 9 is connected to an external network 13 for exchanging inspection data and recipe data with a host computer and other inspection apparatuses.

[Image Pickup Optical System]

A light beam irradiated from a xenon lamp or a mercury xenon lamp is band-limited by a wavelength filter 15a to produce a DUV (Deep Ultra Violet) light beam for illumination. The DUV light beam may have either a broad band of, for example, 200 to 400 nm, or a narrow band of components of a specific bright line. In the case of broad band illumination, color shades due to thin film interference can be suppressed. On the other hand, narrow band illumination allows the optical system to accurately correct the chromatic aberration and therefore raise the resolution.

S polarized light reflected downward by a PBS (Polarizing Beam Splitter) 15 becomes circular polarized light after passing a $\lambda/4$ plate 16. The light beam illuminating a wafer 18 via an objective lens 18 is reflected by the wafer surface and becomes P polarized light after passing the $\lambda/4$ plate 16, and then transmits the PBS. This configuration can prevent the quantity of detected light from decreasing substantially. The reflected light is converged by an image-forming lens 19 onto a linear sensor 20 as an enlarged optical image of the wafer surface. The linear sensor 20 captures the enlarged optical image of the wafer surface and sends the image to an image-processing unit 32 for defect detection. In addition, the detection light path has a branch to a TV camera 21. Connected to an image-processing unit 22, the TV camera 21 is used for alignment and defect review.

Although a lamp is used as the DUV light source in this embodiment, it is also possible to use a high intensity laser light source. For example, a YAG laser (λ=532 nm) can be combined with a non-linear optical element to use the second harmonic wavelength 266 nm.

[Automatic Stage]

The wafer 18, the object to be inspected, is fixed to a wafer chuck 23 by vacuum suction so as to flatten the wafer and prevent it from slipping while the stage is moved. The wafer chuck 23 is mounted on the Z, θ, X and Y stages 30, 24, 25 and 26. The θ stage 24 is controlled immediately after a new wafer is mounted. After the row direction of dies formed in an array is aligned to the scanning direction of the X stage, the θ stage 24 is fixed before inspection is started. During inspection, the X stage 25 moves left to right and the Y stage takes one orthogonal step when the X stages returns. The X, Y and θ stages 24 through 26 are controlled by signals from a stage control computer 27. The position of the X stage 25 is measured by a laser length-measuring device 28. A pixel start timing signal is issued by a timing generator 29 based on the positional information output from the laser length-measuring device 28. The start timing signal is sent to the linear image sensor 20 to read out the image signal.

The stage control computer 27 is connected to the general control unit 9 via the network 13 so that die layout information, etc. can be downloaded for use in positional determination for inspection.

[Image Pickup Operation]

Figure 3:
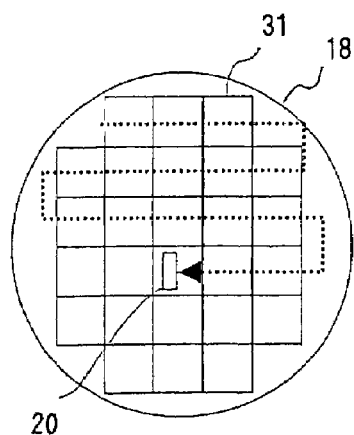
FIG. 3 is a diagram for explaining wafer surface image pickup operation.

The linear image sensor 20 is driven by the start timing signal each time the X stage has traveled a certain distance. A two-dimensional image can be picked up by reading out the linear image sensor 20 in synchronization with this travel distance of the X stage. To secure a high S/N ratio even when the wafer is scanned quickly, a TDI (Time Delay Integration) CCD image sensor may be used for the linear image sensor 20. Constituted by a plurality of one-dimensional image sensors arranged two-dimensionally, the TDI sensor intends to raise the quantity of detected light by delaying the output of each one-dimensional image sensor by a pre-determined period of time so that the output of each one-dimensional image sensor at the same position is added up. FIG. 3 explains how the surface image of the wafer 18 is picked up by the linear image sensor 20. The X stage moves leftward or rightward in the figure at a constant speed while image pickup is done by the linear image sensor 20. At each of the right and left ends, the Y stage 26 takes one vertical step. Each step of the Y stage 26 agrees with the die pitch and therefore the same area of the respective dies is traced by the linear image sensor 20. Reference numeral 31 denotes a die.

[Image Processing]

Figure 4:
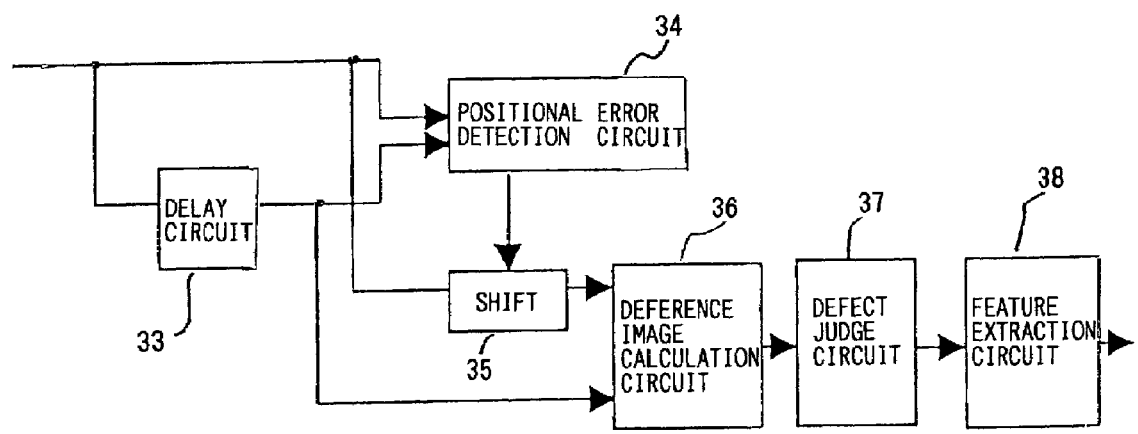
FIG. 4 is a block diagram showing a configuration of an image processing section.

The analog signal output from the linear image sensor 20 is converted to a digital signal by an A/D converted (not shown) and fed to the image-processing unit 32. Using FIG. 4, the following describes the operation of the image-processing unit 32. The input signal is branched into two. One enters a delay circuit. That is, the subsequent processing is carried out using the current signal and a signal delayed in the delay circuit. The amount of delay is selectable by the user to the pitch of any repetitive pattern formed on the die. For example, in the case of die-to-die comparison, the delay is set to the pre-registered die size. If a positional disagreement of image is detected between the two image signals by a positional error detection circuit 34, one image signal is shifted 35. Then, a difference image is created by a difference image calculation circuit 36 and compared by a defect judge circuit 37 with a threshold registered in advance. In a feature extraction circuit 38, defect information, such as the defect's coordinates, size, shape and intensity, is extracted from the image signal of the defective area for later use in grouping after the inspection is complete. The defect information is sent to the general control unit 9 so that it can be stored in a database 12, displayed on the display unit 10 and sent to a host computer via the network 13.

[Automatic Focus System]

Figure 13:
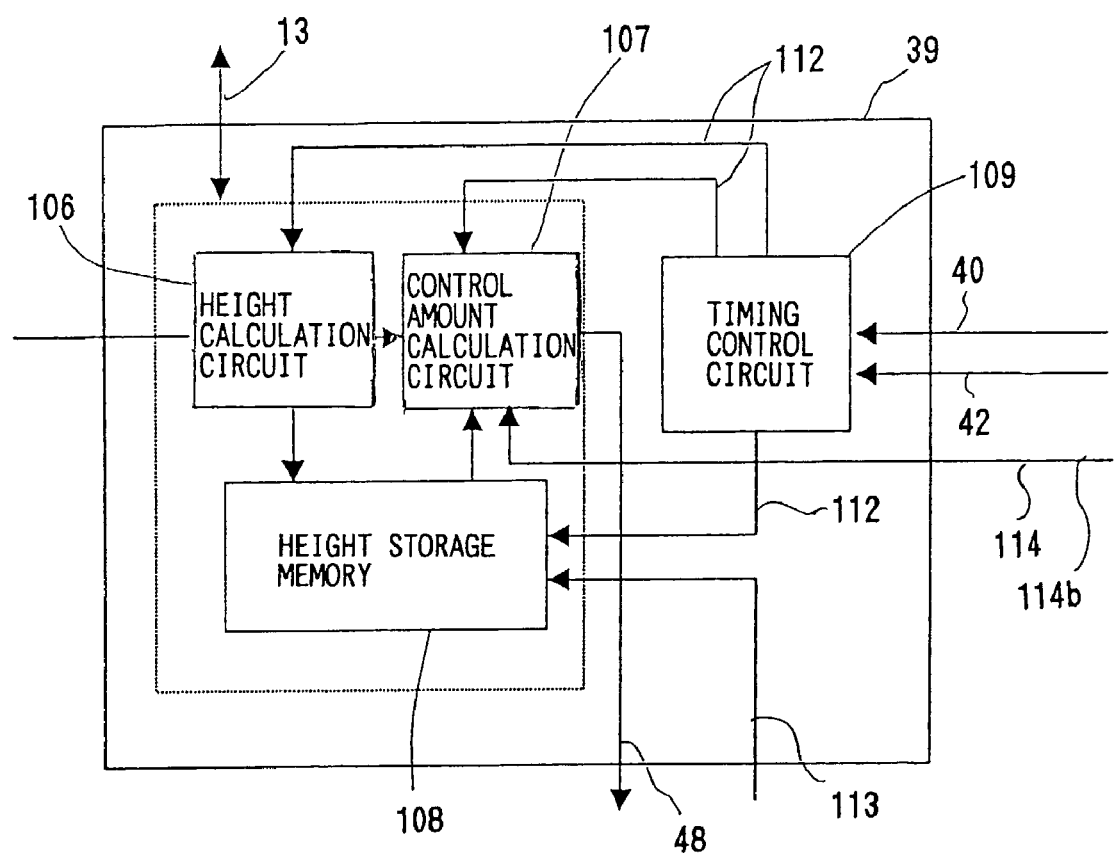
FIG. 13 is a block diagram showing a configuration of an automatic focus computer.

The automatic focus system includes a detection optical system 47 and an automatic focus computer 39. The detection optical system 47 detects the heights of several points around the current image pickup position and sends the detection signals to the automatic focus computer 39. As shown in FIG. 13, the automatic focus computer consists of a height calculation circuit 106, a control amount calculation circuit 107, etc. and, based on the difference between the detected height and the preset control target, calculates a control amount 48 to control the Z stage 30. Via the network 13, the automatic focus computer 39 is connected to the general control unit 9 which switches the operation mode to and from inspection mode, review mode or the like and sends/receives automatic focusing recipes. In addition, receiving a die start signal 40 and a stage return signal 41 from the stage control computer 27 and TDI shift pulses from the timing generator 29, the automatic focus computer 39 uses them in the timing control circuit 109. Further, it receives highly realtime signals 43 such as auto focus ON/OFF at inspection from the stage control computer 27 via the DIO. The operation of the automatic focus computer 29 will be described in detail later.

Figure 5:
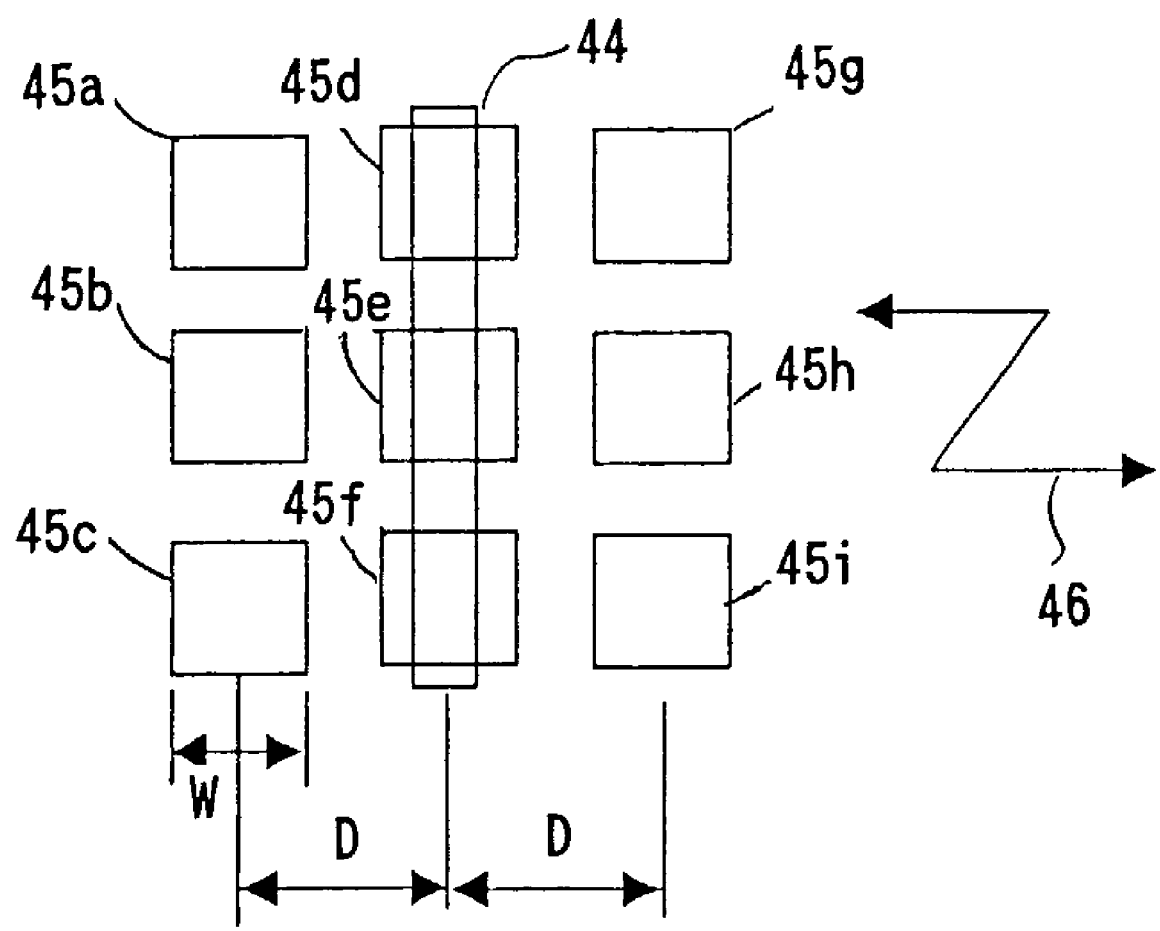
FIG. 5 is a diagram showing the relation between the image pickup area and height detecting positions.

Then, referring to FIG. 5, the following describes a particular aspect of the present invention, that is, the relation between the image pickup range of the linear image sensor 20 and the height detecting positions of the detection optical system 47 in the automatic focus system according to the present invention. An image pickup range 44 is the range detected by the linear image sensor 20 at a time. The height detection means (detection optical system) 47 detects the average height of each range which includes one of several points (45a through 45i) around the current image pickup position. Each range has a width W in the scanning direction 46 as shown in the figure. More preferable height detection means 47 will be described later in detail. The height detection points (45a through 45i) are characterized in that they are symmetrical about the image pickup range in the stage scanning direction 46. In the figure, the height detection points (45a through 45i) are distant from the image pickup position 44 by D in the X stage scanning direction 46. In addition, height is detected at several points also in the direction orthogonal to the stage scanning direction 46 to cope with steps in the orthogonal direction.

Figure 6:
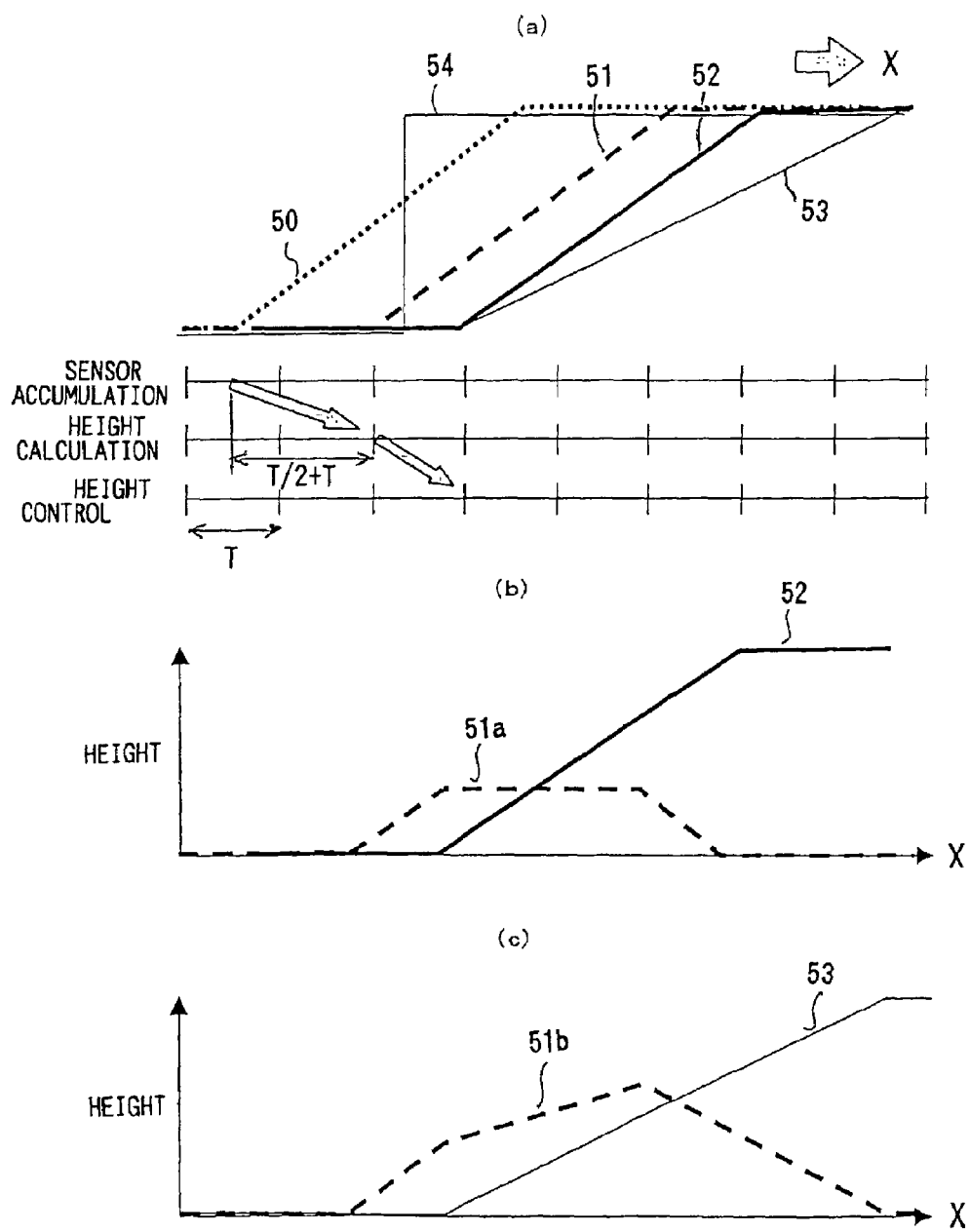
FIGS. 6(a) through 6(c) are diagrams for explaining automatic focusing operation around an up-step.

Then, the following describes how automatic focusing is done when an up step is scanned with reference to FIG. 6. Consisting of three steps: height detection by the sensor 205 of the automatic focus detection optical system, height calculation executed by the automatic focus computer 39 and sample positioning height control, the automatic focusing operation is executed in synchronization with the timing signal 113 having a period T. As shown in the figure, detection by the sensor 205 is executed successively during a period T. To calculate a height based on the signal, another period T is spent. Further, one more period T is needed for height control. The height detected by the sensor 205 is the average height of an area of the sample which passes the height detecting position during a period T and can be considered as the height of the sample detected at T/2. Accordingly, it takes T/2+T until the height calculation is completed since the corresponding detecting operation of the sensor and another T until the height control is completed for the calculated height.

A broken line 50 is the locus of heights detected by the sensor 205, a broken line 51 is the locus of calculated heights and a solid line 52 is the locus of focal points when the sample is actually controlled in height. The response of the height control is dependent on the performance of the Z stage 30. If the Z stage can follow the change in the height calculation result, the slope of the solid line 52 agrees with that of the broken line 51. If not, the height control delays as shown by a solid line 53.

As described above, for accurate focusing, quick response of the Z stage 30 is important in addition to accurate height detection. Accordingly, the Z stage 30 in FIG. 2 should have a high response actuator, such as a linear motor, a voice coil, and other elements designed suitably. Alternatively, lifting the objective lens may also be feasible because its inertia is small.

Anyway, in such a high-resolution optical system using a DUV light source as shown in FIG. 2, performance of the automatic focusing mechanism is particularly important. The resolution RES and depth of focus DOF of the optical system are given by the following equations 1 and 2:

$$RES=0.5\times\lambda/NA \quad \text{(Equation 1)}$$

$$DOF=\pm 0.5\times\lambda/(NA^2) \quad \text{(Equation 2)}$$

Shortening λ to raise the resolution results in narrowing the depth of focus. For example, DOF=±208 nm when λ=266 nm and NA=0.8. On the other hand, Al wiring patterns formed on a semiconductor wafer are sometimes thicker than 500 nm, leaving steps whose heights exceed the depth of focus.

This indicates that the error induced by a pattern step may be as significant as the error induced by transparent film and the error induced by discontinuous reflectance which are also described in FIG. 1. It is necessary to suppress these errors so that the wafer surface can be controlled to within the depth of focus. Method for reducing these errors will thereinafter described.

First, a description will be made of methods for reducing the error induced by a pattern step. Although pattern steps are cited as examples, the same effect can also be expected when they are applied to the die's peripheral scribe line having a larger height change.

FIG. 7 is a diagram for explaining why defocus occurs around step boundaries. A broken line 62 is the locus of detected heights and a broken line 61 is the locus of controlled focal positions. Since the average height in the detection range is detected at the step boundaries as noted in FIG. 6, the locus of detected heights begins to gradually rise when the step reaches the detection range W and agrees with the step surface when the whole detection range is covered by the step surface. The locus also changes gradually in the down-step area. Therefore, the pattern surface gets out of focus in the up-step and downstep defocus areas 60 as shown in FIG. 7(*a*), resulting in a defocused pattern image 63 picked up. A method for reducing such defocus in pattern boundaries is disclosed in Japanese Patent Laid-Open No. 7-86135. In this method, height information ahead of the image pickup position is used for focusing. That is, when the stage is moved rightward as shown in FIG. 5, height information obtained on the right side of the image pickup position is used for focusing. A broken line 65 in FIG. 7(*c*) is the locus of heights detected in this method. Although this method can prevent defocus in the up-step area, however, defocus of the step surface is enhanced in the down-step area as indicated by reference numeral 63.

Then, a description will be made of a first focusing method of the present invention with reference to FIG. 8. A thin broken line 66 in FIG. 8(*a*) is the locus of heights detected in this method. Thick broken lines in the figure are the loci of heights detected respectively at three points arranged in the scanning direction (for example 45*a*, 45*d* and 45*g* in FIG. 5). Of the heights detected at these three points, the maximum value is assumed as the representative height. As shown, although the detected height changes gradually in the height detection area W, the pattern surface height can accurately be detected in both up-step and down-step areas since the maximum value in the ±D region around the image pickup position 44 is employed. Further, the locus of detected heights in the up-step area is symmetrical to that in the down-step area, not depending on the scanning direction of the X stage. Therefore, any part of the step surface can be focused as shown in FIG. 8(*b*).

Figure 8:
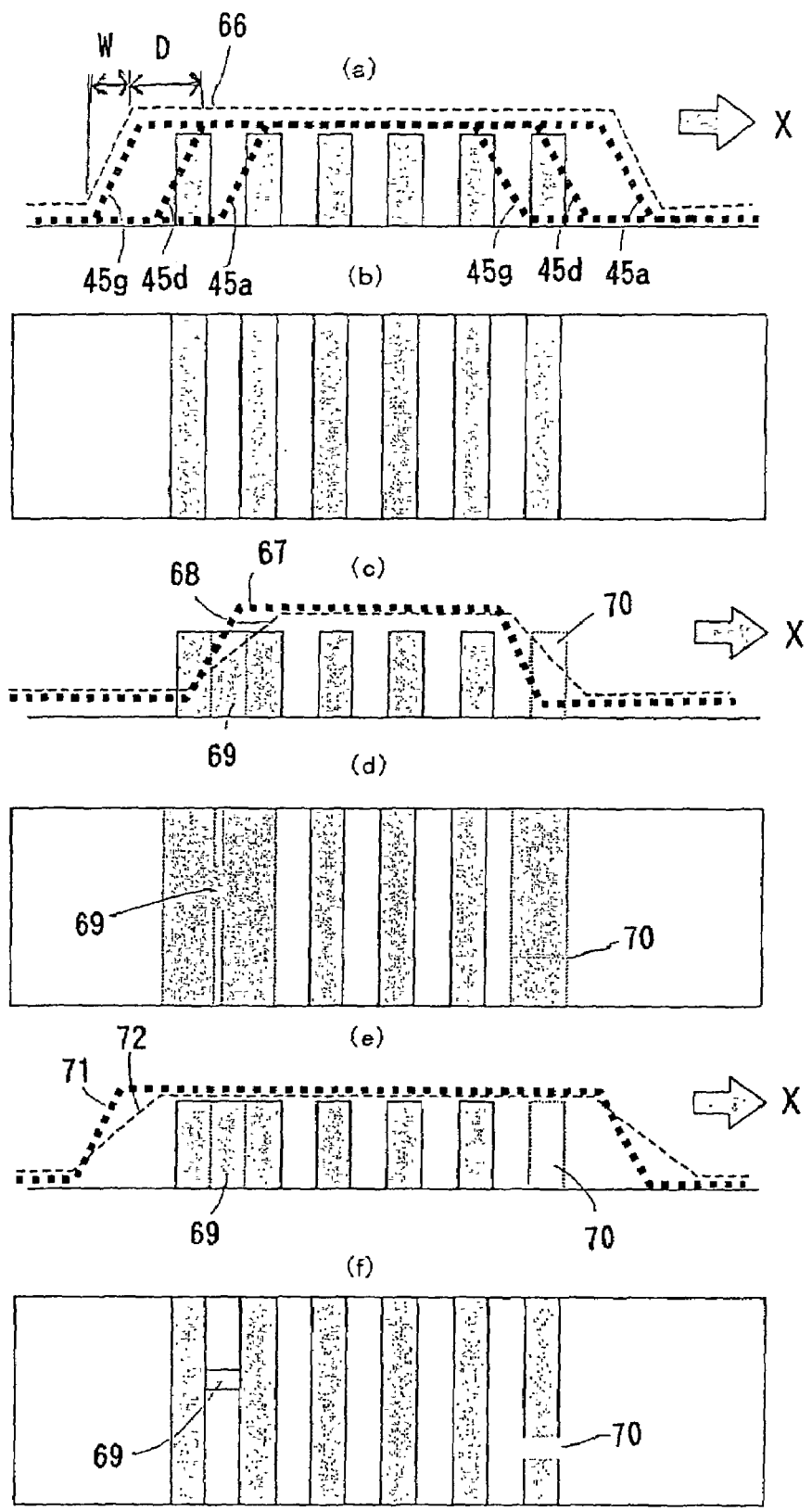
FIGS. 8(a) through 8(f) are diagrams for explaining a first focusing method according to the present invention.

In FIGS. 8(*c*) through 8(*e*), an image pickup result obtained by the conventional method is compared with that by the method of the present invention. The sample has pattern defects around step boundaries. A broken line 67 and a solid line 68 are the respective loci of detected heights and focal positions in the conventional method. Both a short 69 in the up-step area and an open 70 in the down-step area are defocused. On the other hand, in the case of the focusing method according to the present invention, both defects are captured as clear images as shown in FIG. 8(*f*). If these images are applied for defect detection, it is possible to detect defects around step boundaries without overlooking any of them. In the first method of the present invention, defocus occurs in the up-step and down-step areas and the uneven wafer surface is not completely followed. However, it is noteworthy that this method does not fail to focus any part of the pattern surface. Therefore this method can be used suitably as the means to detect defects which are caused by the final process to the object under inspection such as a semiconductor wafer which involves multi-layer formation.

Then, a description will be made of the application of the first focusing method of the present invention to semiconductor wafer inspection apparatuses showing remarkable advance in inspection speed.

To raise the inspection, it is necessary to shorten the image pickup time by raising the scanning speed of the X stage. To keep the pattern surface focused under such a condition, follow ability of the Z stage is critical. Using FIG. 8(*b*), the following describes a Z stage control method designed so that the first focusing method of the present invention can be implemented. FIG. 8*b*(*a*) is an ordinary control function for the Z stage. The horizontal axis represents the deviation of the detected height from the control target. When the control target is followed by the Z stage, the horizontal value is almost zero 501. If not, the horizontal value is large in magnitude. It is said that the control target is followed by the Z stage when the wafer surface is in the depth of focus and a clear image is picket up. The vertical axis represents the amount of control for the Z stage. As shown, the Z stage is not moved when the deviation shown in the horizontal axis is almost zero. The amount of control to move the Z stage is increased in proportion to the magnitude of the deviation.

Its proportionality coefficient (inclination of the straight line 502) is the control gain and designed to be as near to 1 as possible depending on the stability of the Z stage drive system. If the deviation exceeds a certain level, the Z stage is moved in steps of the maximum amount 503 allowed to the Z stage. A point in the quadrant I indicates the detected height is larger than the control target, that is, the wafer surface is above the focal position. In this case, the Z stage is driven downward. A larger horizontal value means a higher wafer height while a larger vertical value means a larger amount of control to drive the Z stage downward. FIG. 8b (c) shows the locus 504 of heights detected from a wafer having a step and the locus 505 of focal positions obtained as a result of driving the Z stage according to the control function of FIG. 8b(a).

If the response of the Z stage is too slow, the step surface may be picked up before the focal position is moved to the step surface, resulting in defocus 506. In the present invention, this problem is solved by controlling Z stage according to the control function shown in FIG. 8b(c). This control function is characterized in that the Z stage drive amount in the quadrant III is smaller than in the quadrant I. That is, although the Z stage is controlled downward by the maximum gain of the system in the same manner as conventional, the gain for upward control is intentionally designed to be smaller than the maximum gain.

FIG. 8b (d) shows the control result obtained by this method of the present invention in comparison with (b). In the first up-step area, defocus 506 occurs in the same manner as the conventional method. However, the Z stage does not rise completely due to the effect of the quadrant III. Therefore defocus in the next up-step area 507 can be prevented since the pattern surface can quickly be focused.

Figure 9:
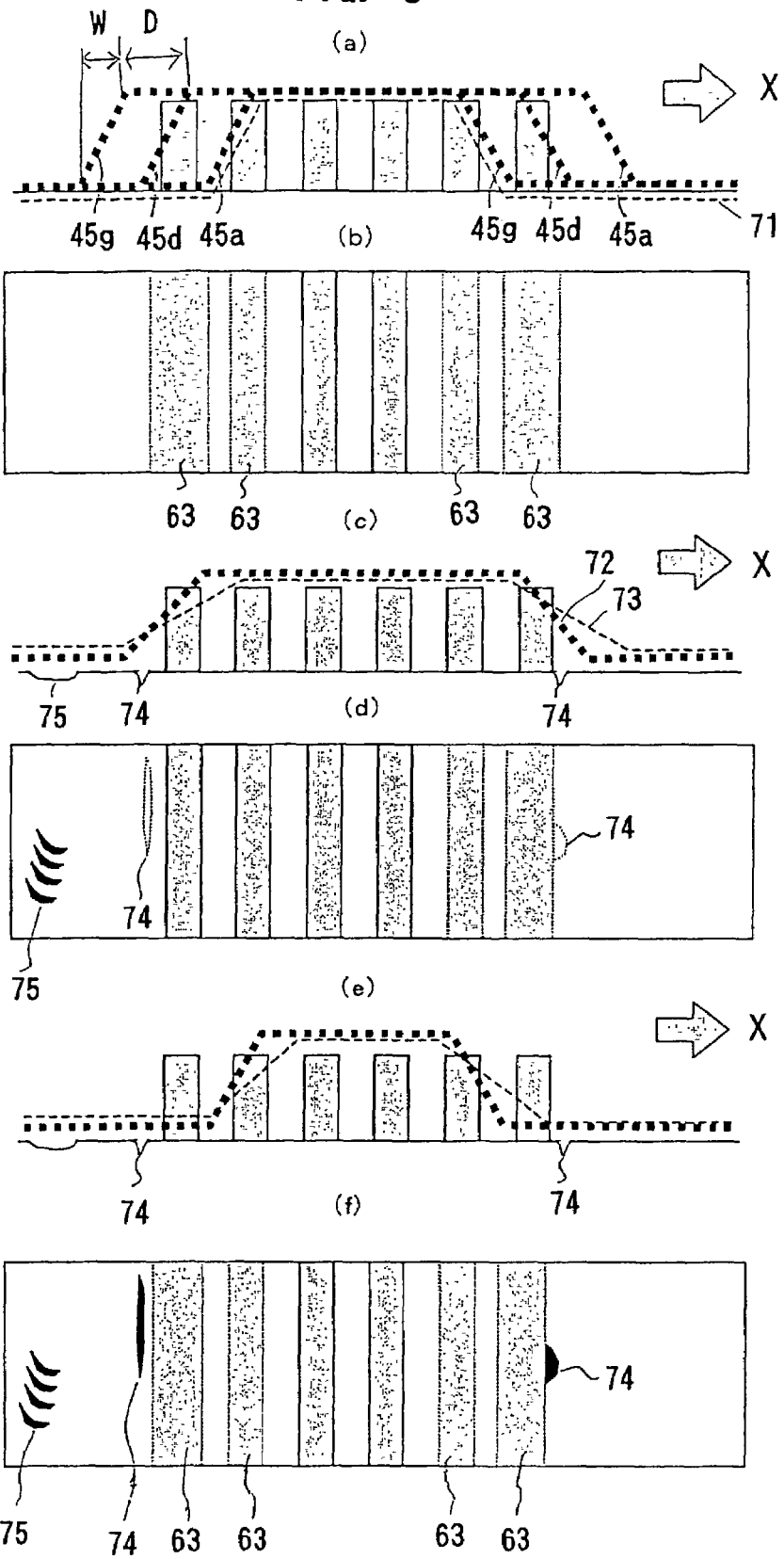
FIGS. 9(a) through 9(f) are diagrams for explaining a second focusing method according to the present invention.

Then a second focusing method according to the present invention is described using FIG. 9. This second method can be used suitably to detect defects which exist on the interlayer insulation film below the pattern layer. The inter-layer insulation film may have scratches 74 and 75 as a result of planarization by CMP (Chemical Mechanical Polishing). Scratches 74 and 75 are critical defects because they may cause a short and open in the pattern layer. In FIG. 9(a), a thin broken line is the locus of detected heights. Thick broken lines in the figure are the loci of heights detected respectively at three points arranged in the scanning direction (for example 45a, 45d and 45g in FIG. 5). Of the heights detected at these three points, the minimum value is assumed as the representative height. As a result, this method does not fail to focus any part of the no-pattern lower surface.

In FIGS. 9(c) through (e), the image pickup result obtained by prior art is compared with that by the second focusing method of the present invention. On the inter-layer insulation film, there are scratches near the step boundaries. Broken lines 72 and 73 in FIG. 9(c) are the respective loci of detected heights and focused positions by prior art. The scratches 74 existing respectively just before the up-step area and just after the down-step area are defocused. On the other hand, in the case of the focusing method according to the present invention, these defects 74 and 75 are captured as clear images as shown in FIG. 9(f). If these images are applied for defect detection, it is possible to detect defects around step boundaries without overlooking any of them.

Then a third focusing method of the present invention will be described with reference to FIG. 10. This third method can be used suitably to inspect the bottoms of gorges formed by pattern etching. Etching process may leave a critical etching residue 80 between patterns, causing a pattern short. Detection of such critical defects must be done in every area where pattern etching is done. In FIG. 10(a), a thin broken line is the locus of detected heights. Thick broken lines in the figure are the loci of heights detected respectively at three points arranged in the scanning direction (for example 45a, 45d and 45g in FIG. 5). Of the heights detected at these three points, the maximum height is taken. The representative height is calculated by subtracting the pattern height from the maximum value. As a result, this method does not fail to focus any pattern gorge.

In FIGS. 10(c) through (e), the image pickup result obtained by prior art is compared with that by the third focusing method of the present invention. There are etching residues 80 in pattern-to-pattern gorges. Broken lines 78 and 77 in FIG. 10(c) are the respective loci of detected heights and focused positions by prior art. The etching residue defects 80, including the one just after the up-step area, is defocused. On the other hand, in the case of the focusing method according to the present invention, these defects 80 are captured as clear images as shown in FIG. 10(f). If these images are applied for defect detection, it is possible to detect defects in pattern gorges without overlooking any of them.

Figure 10:
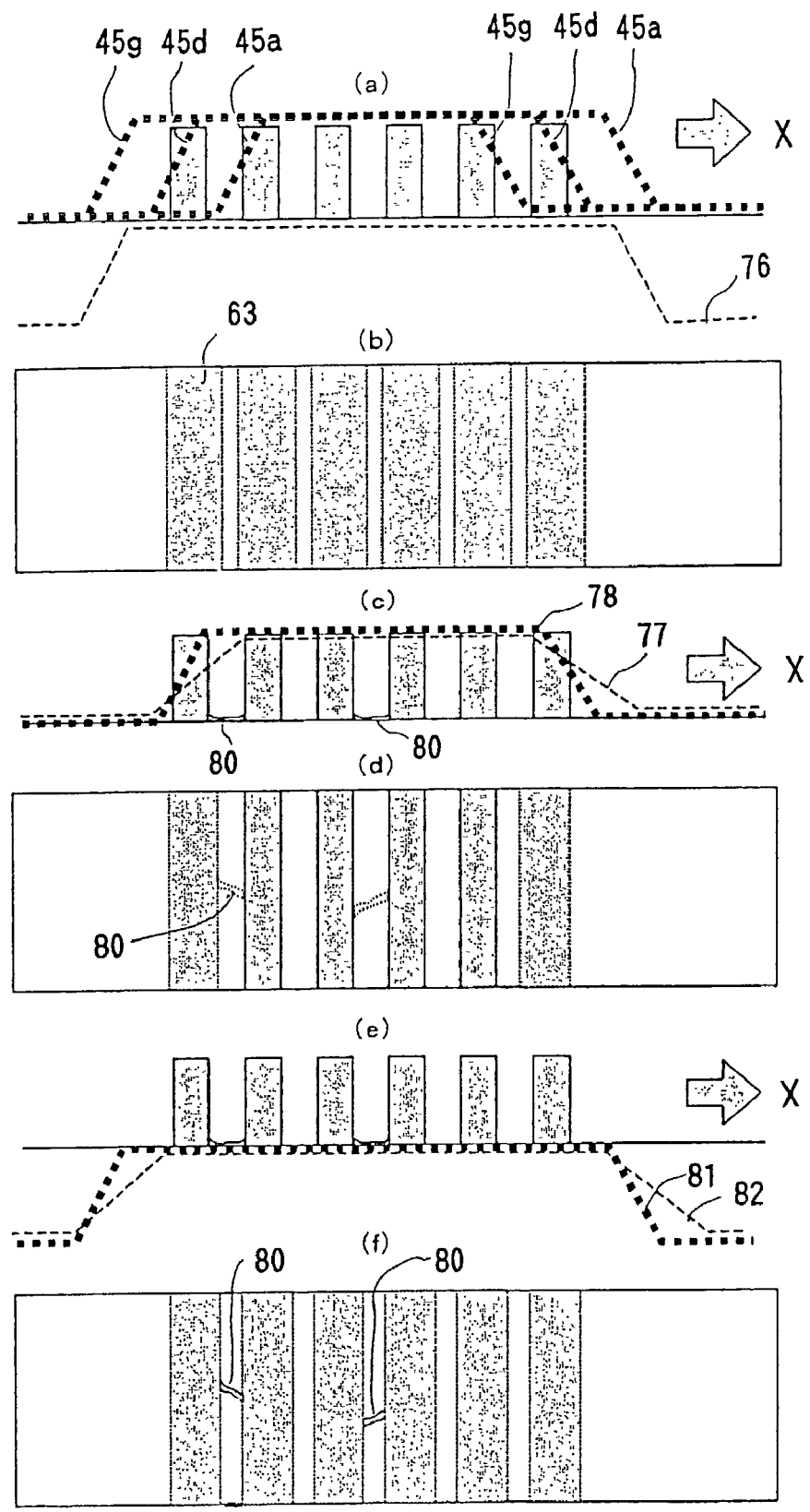
FIGS. 10(a) through 10(f) are diagrams for explaining a third focusing method according to the present invention.

Therefore, the embodiments of the present invention described so far with reference to FIGS. 8 through 10 are characterized in that they can clearly detect the defects 69, 70, 74, 75 and 80 around and at step boundaries which are formed by a process of concern.

Referring to FIG. 11, the following describes a condition setting screen provided by the general control unit 9 to allow the user to specify focusing conditions to the automatic focus computer 39 according to the embodiments described above. Into a focusing condition setting screen of FIG. 11(a) displayed on the displayed unit 10, the user designates a product 301 and process 302 of concern for edit. The pertinent data is read in and the product name and process name are displayed. Then the user chooses a screen from the screen menu (Automatic Inspection 303, Defect Check 304, Condition Set 305 (consisting of Layout Set 305a, Automatic Focus Set 305b and Threshold Set 305c)). In the figure, the Condition Set screen 310 is selected and its sub screen Automatic Focus Set 305b is selected. From Automatic Focus Set 305b, Height Calculation Rule 305ba is now selected.

Height Calculation Rule 305ba allows the user to specify how to calculate a representative height from a plurality of heights detected around the image pickup position as described in FIGS. 8 through 10. Max is selected to inspect the surface of the pattern layer without overlooking defects there. To accurately inspect the layer below the pattern layer, Min is selected. If it is already known that the process of concern, such as CMP, leaves step-free flat surface, Average is selected since averaging a plurality of detected heights provides stable surface height detection. In addition, this Height Calculation Rule 305ba allows the user to define another height calculation rule.

In the screen 310 of FIG. 11(a), a wafer map (100) and an enlarged view (101) of a die in the wafer are displayed. FIG. 11(b) is another example contents of the focusing condition setting screen. The screen of FIG. 11(b) allows the user to determine which height calculation rule provides the most reliable defect detection by means of comparison. Shown left is a defect map (101a) of a specific die created based on the image pickup result obtained by using the height detection rule Max. As shown, layout data (102) is displayed additionally in order to facilitate the user to identify patterns having defects. Created based on CAD data, the layout is shown as a block diagram of patterns sorted by function and process. Right shown is a defect map (101*b*) of the same die created by using a different height calculation rule. By comparing defect maps which were created by applying different height calculation rules, it is possible to select an appropriate height calculation rule for the process of concern. According to the defect map (101*a*) by the Max rule and the defect map (101*b*) by the Average rule in FIG. 11(*b*), the Max rule provides higher defect detection sensitivity around pattern boundaries. It is also possible to compare defect maps which have been created by applying different offsets instead of different calculation rules. After selecting an appropriate height calculation rule, the user hits the Register button to register it to the recipe.

Then, referring to FIG. 12, the following describes a focus map used in a fourth focusing method of the present invention. This focus map 330 may be prepared either by the automatic focus computer 39 or the general control unit 9. The focus map 330 shows a distribution of detected height Y in the two-dimensional (X, Y) table. Obtained by scanning a die, it consists of a (X, Y, Z) data array. FIG. 12(*b*) is a bird's eye view of a focus map created by scanning a die pattern of FIG. 12(*a*). FIG. 12(*c*) shows a focus map preparation procedure. Data is obtained by scanning the same die leftward and then rightward. Then calculation is made between the two results to create a focus map. This is because the locus of heights detected at step boundaries differs depending on whether the die is scanned leftward or rightward. The procedure may also be designed in such a manner that the data obtained by leftward scan and that by rightward scan are registered separately into the internal memory 108 or the like for later selective use depending on the scanning direction selected. In the figure, a broken line (103) is the locus of detected heights and a broken line (104) is the locus of focal levels. A solid line (105) is the result of taking the larger height at each point where height detection was done in both scanning directions. The locus (103) of detected heights and the locus (104) of focal levels are calculated separately. Stored as two-dimensional data into, for example, the height storage memory 106, the calculation results will be used as a focus map 330. Usefulness of focus maps will be described later in detail.

Then, referring to FIG. 13, the following describes the automatic focus computer 39 of the present invention. FIG. 13 is a block diagram showing an embodiment of the automatic focus computer 39 according to the present invention. The automatic focus computer 39 consists of a height calculation circuit 106, a control amount calculation circuit 107, a height storage memory 108 and a timing control circuit 109. When a focus map is prepared, the wafer height and the displacement of the Z stage at the same point are calculated respectively by the height calculation circuit 106 and the control amount calculation circuit 107 and stored into the height storage memory 108 every one or several operation periods given by the timing control circuit 109 while a specific die is scanned by the X stage 25. The timing control circuit 109 receives a die start signal 40 from the stage control computer 27 and a TDI shift pulse 42 from the timing generator 29. Initiated by the die start signal 40, the timing control circuit 109 counts the TDI shift pulse 42 and generates a timing control signal 112. For synchronization, this signal 112 is sent to the height calculation circuit 106, the control amount calculation circuit 107 and the height storage memory 108. As the result, height calculation, Z stage control and Z stage position read can be performed for the same point in the die. The signal output from the height calculation circuit 106 is a broken line 51*a* in FIG. 6(*b*) and the output of the control amount calculation circuit 107 is a solid line 52 in FIG. 6(*b*). Adding the two outputs results in wafer step profile data, a broken line 51 in FIG. 6(*a*). It is possible to read in the Z stage position (113) and substitute it for the output of the control amount calculation circuit 107. The stored focus map is sent via the network (13) to the general control unit 9 where focus maps are maintained as recipe data sorted by product type and process.

When using a focus map 330, the focus map is downloaded from the general control unit 9 into the height storage memory 108. In this case, the automatic focus computer 39 reads out focus map data associated with the current position, compares it with the calculated height and calculates the Z control. Then a control signal 48 based on the calculated control amount is sent to the Z stage 30. The control amount calculation circuit 107 receives a return die judge flag 114 and a scan direction judge flag 114*b* from the stage control computer 27. Focus map read-out, height calculation, control amount calculation and Z stage position read-out are synchronized with the timing signal 112 so that the images of the dies to be compared for inspection can be picked up under the same condition.

Then, referring to FIG. 14, the following describes a fourth focusing method according to the present invention. In this fourth method, pattern images are picked up with the focal position held at a preset level not subject to the unevenness of the die patterns. Due to this, defects in a specific pattern of concern can be detected selectively. FIG. 14(*a*) is the locus of detected heights recorded in the focus map. In FIG. 14(*b*), a pattern height to be detected is defined. This figure indicates that the pattern surface height (115) is to be always detected at any point of the die. FIG. 14(*c*) shows an offset map calculated from FIG. 14(*b*). For the height in FIG. 14(*b*) to be detected at any point of the die, the offset must be changed depending on the coordinates (X, Y) of each height detection point. Therefore, the offset shown in FIG. 14(*c*) is calculated in advance by the automatic focus computer 39. Like the focus map, the offset map is also stored in the height storage memory 108 shown in FIG. 12. FIG. 14(*d*) shows the height detection result obtained by using the offset map in FIG. 14(*c*). The surface level of the sample is controlled based on the result of adding the offset of FIG. 14(*c*) to the height detection result (116). To exclude the influence of the acting delay of the Z stage, the locus of focal positions is used instead of the locus of detected heights in FIG. 14(*a*).

Figure 15:
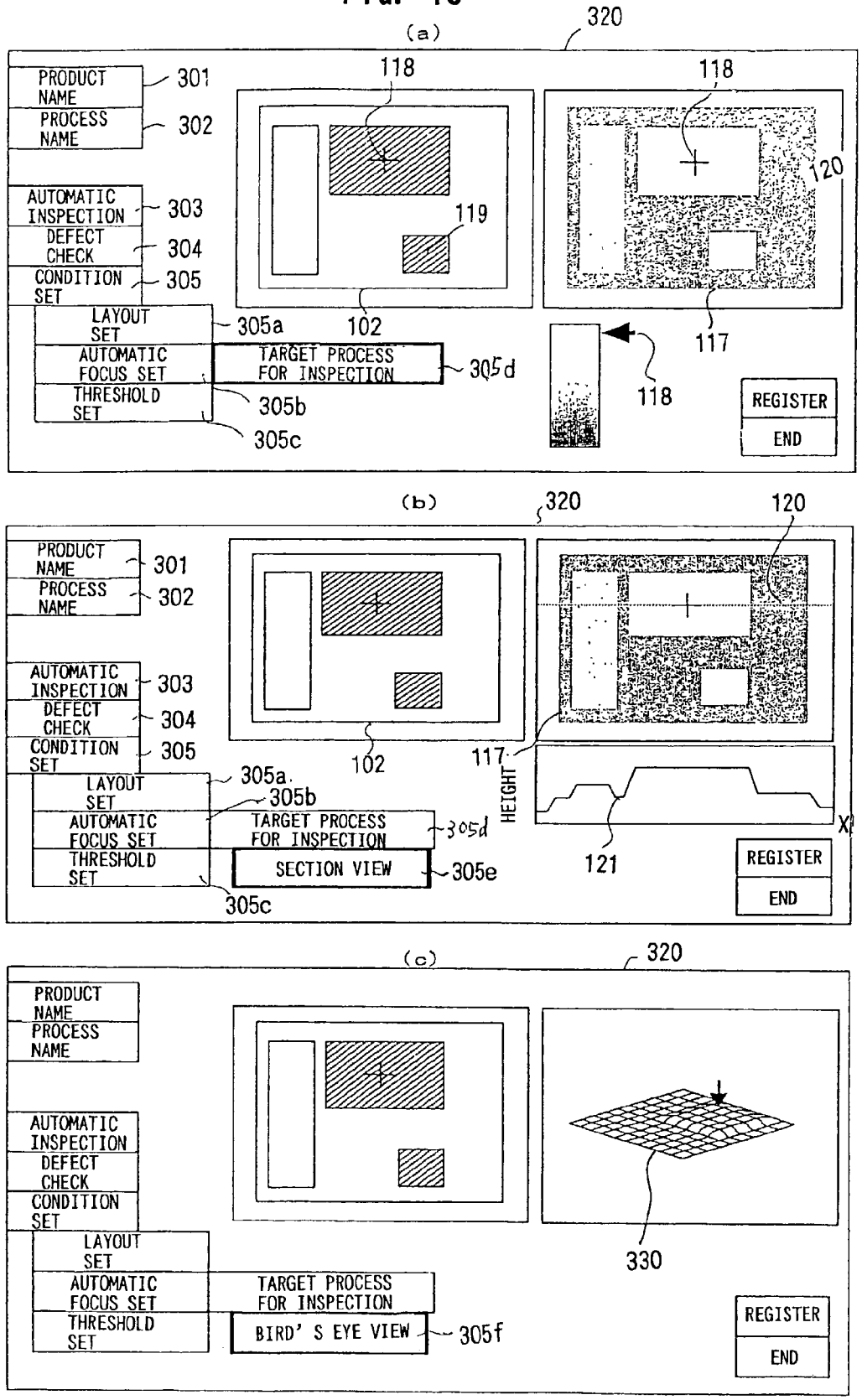
FIGS. 15(a) through (c) show inspection recipe setting screens using a focus map.

Then, referring to FIG. 15, a description will be made of setting of an inspection recipe by using a focus map 330 on the general control unit 9 or automatic focus computer 39 of a defect detection apparatus according to the present invention. FIG. 15 shows an inspection recipe-setting screen 320 on the display unit 10. Each button's function in FIG. 15(*a*) has been described in FIG. 11. In the screen, the die's internal layout 102 and focus map 117 are displayed as two-dimensional images. The focus map 117 is a shaded image where the degree of shading represents the height. Using a cursor 118 displayed in the layout section or the focus map, the user can select a specific pattern block or a focusing height. The cursor in the layout section, that in the focus map and that in the graduation indictor move consistently with each other. After selecting a height for focusing, the user hits the Register button to register the recipe with the product type and process name displayed. A hatched frame 119 in the layout section shows which patterns are to be inspected for defects if the selected height is kept in focus. FIG. 15(*b*) is another example of the inspection recipe setting screen. One scan profile data 121 along a position 120 selected by the cursor is displayed. In FIG. 15(*c*), the focus map 330 is displayed three-dimensionally as a bird's eye view. This three-dimensional indication facilitates the user to select a height to be kept in focus.

Figure 16:
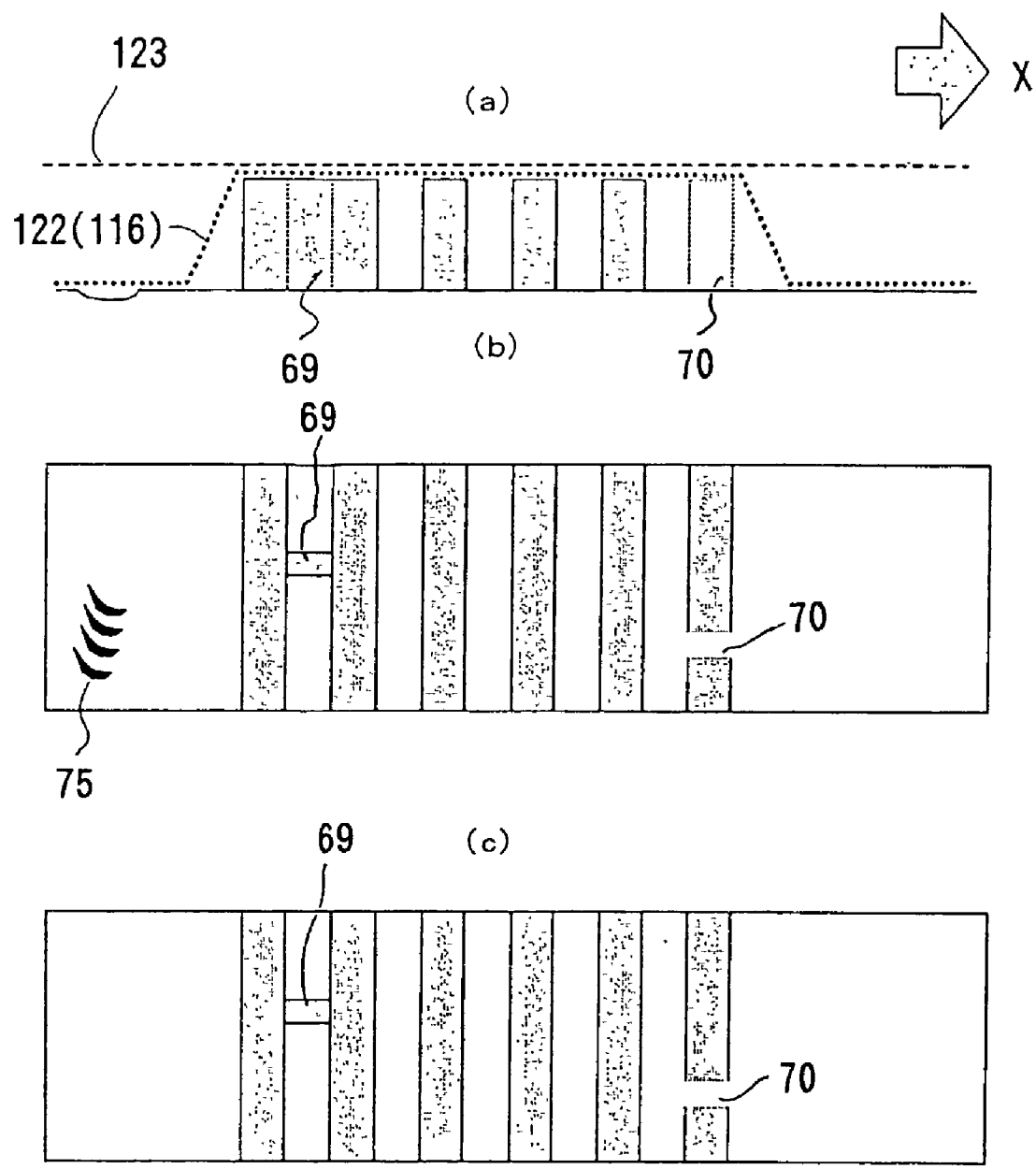
FIG. 16(a) shows the results of detected heights 122 and the locus 123 of points controlled to be in focus by the fourth focusing method.
FIG. 16(b) is an image obtained when the focus is moved along the dotted line 122 of (a)
FIG. 16(c) is an image obtained when the focus is moved along the dotted line 123 of (a)

Then, referring to FIG. 16, a description will be made of an effect of the fourth focusing method of the present invention described earlier. In FIGS. 16(*a*) through (*c*), a pattern image captured by the fourth method is compared with an image obtained by prior art. The pattern has a plurality of defects. A broken line 122 (116) is the locus of detected heights and a broken line 123 is the locus of points controlled to be in focus by the fourth focusing method. If the focal height moves along the broken line 122, not only a pattern open 70 and a pattern short 69 but also a scratch defect 75 on the surface of the inter-layer insulation film are detected. In the case of this embodiment of the present invention, only the pattern defects are captured clearly while the scratch defect 75 on the lower surface is defocused since the pattern surface is kept in focus. If this method is applied to an defect detection apparatus, it is possible to selectively inspect a specific pattern for defects and therefore facilitate the identification of processes which causes defects, resulting in quick troubleshooting of imperfect processes.

Then, a description will be made of a method for securing the same image pickup condition to each pattern formed repeatedly on the sample. This allows high sensitivity detection of micro-defects in a defect detection apparatus where detection is done by comparing patterns. When an identical focusing error occurs at both dies to be compared, the comparison does not detect false difference. If a focusing error occurs at only one of the dies to be compared, false defect detection may occur. To prevent this false detection, the apparatus must be configured in such a manner that the same focusing condition is secured for the dies to be compared.

Figure 17:
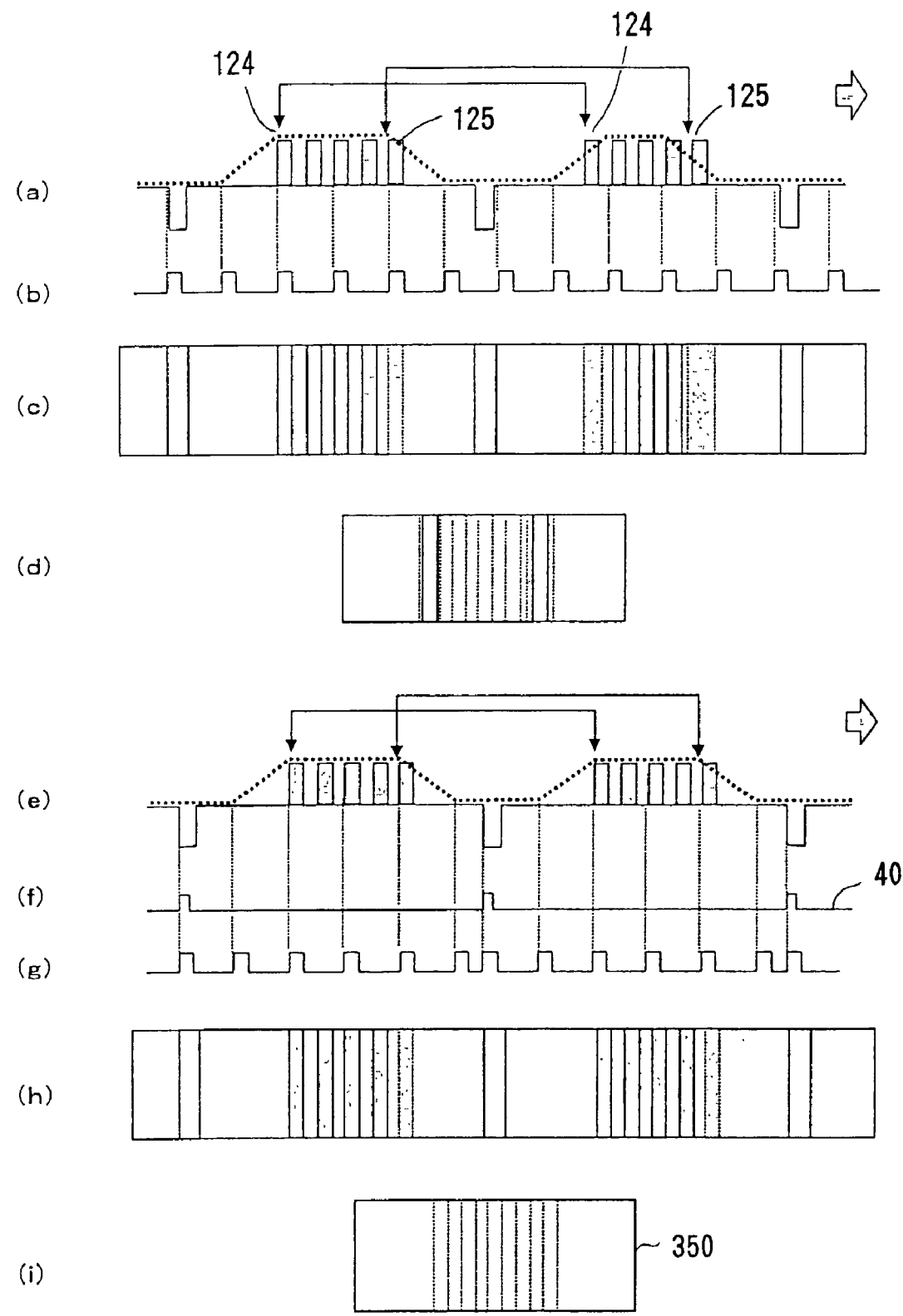
In FIGS. 17(a) through (d), focusing is not executed at the same relative position of each chip.
FIGS. 17(e) through 17(i) show that focusing is executed at the same relative position of each chip.

An embodiment of an automatic focus computer 39 according to the present invention is described with reference to FIG. 17. In this embodiment, focusing is made at the same relative position of each die. In the case of FIGS. 17(*a*) through (*d*), focusing is not made at the same relative position of each die. FIG. 17(*a*) is the locus of focal points and FIG. 17(*b*) shows the operation timing signal. The signal in FIG. 17(*b*) is generated, for example, within the automatic focus computer and is independent of the position of the X stage. Height detection and Z stage control are done in synchronization with this signal. Each arrow pair indicates the same relative position of two dies. See the pattern start point (124). Apparently between the left and right dies, there is a difference of the height detection timing relative to the pattern start point. Due to this, in the detected image of FIG. 17(*c*), the pattern of the right die is defocused while the pattern of the left die is in focus. Also at the pattern end point (125), there is a difference in the focal condition between the left and right dies. As a result, the difference image in FIG. 17(*d*) shows disagreements at the pattern start and end points, causing false defect detection.

In the case of the embodiment of the present invention, focusing is made at the same relative position of each die as shown in FIG. 17(*e*) through (*i*). FIG. 17(*e*) corresponds to FIG. 17(*a*) and shows the locus of focal points. FIG. 17(*g*) shows the operation timing of the height detection means 47. FIG. 17(*f*) is a die start signal 40 asserted based on the position of the X stage. This embodiment is characterized in that a pulse 42 is synchronized with the die start signal 40. Therefore, height detection can be done at the same timing relative to the pattern start position in each of the left and right dies. As shown in FIG. 17(*h*), the images of the pattern start and end points can therefore be captured under the consistent focal condition. As a result, a difference image 350 has no disagreement there as shown in FIG. 17(*i*).

Figure 18:
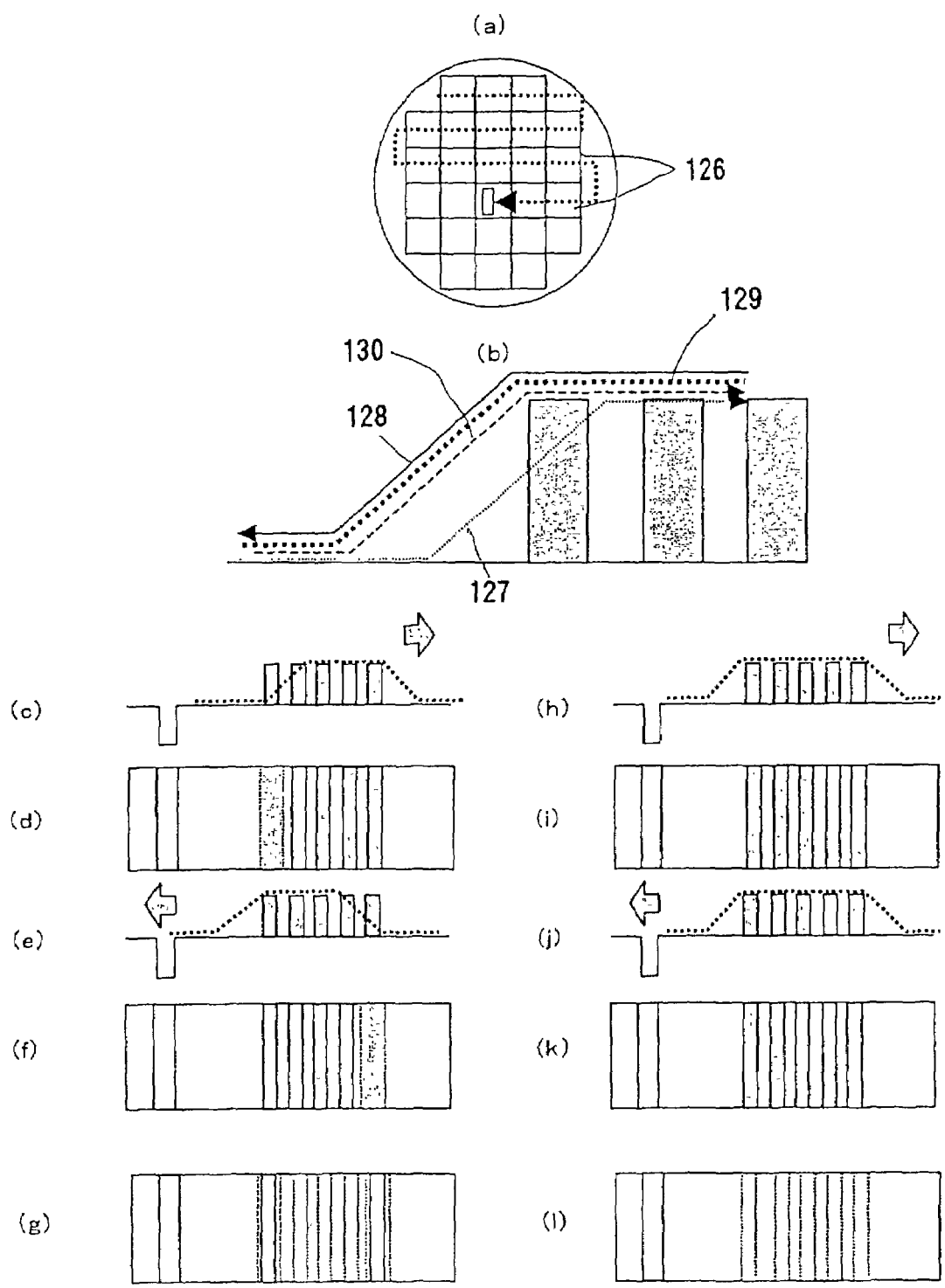
FIG. 18(a) is a top view of a wafer showing how the wafer is scanned where the scanning direction is changed and FIG. 18(b) is a sectional view of the wafer with scanning directions indicated.
FIGS. 18(c) through 18(g) are results of a conventional method.
FIGS. 18(h) through 18(l) are diagrams for explaining a method of the present invention.

Then, referring to FIG. 18, the following describes another embodiment of the automatic computer 39 according to the present invention. This embodiment intends to solve the problem that the height detecting condition differs between two dies which exist where the stage is turned back. Two vertically adjacent dies must be compared when the stage reaches the turning point as shown in FIG. 18(*a*). These dies are scanned in opposite directions and the detected height error depends on the scanning direction, causing a false disagreement. In addition, the movement of the stage may further enhance the disagreement since the locus of detected heights does not agree with that of focal points if the response is slow as described with FIG. 6.

In the case of this embodiment, the focus map 330 is used to make identical the loci of detected surface heights of the dies scanned in opposite directions. In FIG. 18(*b*), a broken line 127 is the locus of focal points obtained by scanning the left to right while a broken line 128 is the locus of focal points by right to left scanning. These two loci do not agree with each other at the step boundary, perhaps resulting in false defect detection.

In this embodiment, therefore, data in the focus map 330 are used as surface heights where the difference between the detected heights and the corresponding data in the focus map 330 is larger than threshold. As a result, since focusing control is done according to the focus map's locus (a broken line 130) when the pattern is scanned left to right, false defect detection can be reduced in compare inspection.

In prior art, false defect detection may occur at the step boundary as shown in FIGS. 18(*c*) through (*g*) since the focusing condition differs. (*c*) is the locus of focal points by rightward scanning. (*d*) is an image picked up along the locus (*c*). (*e*) is the locus of focal points by leftward scanning and (*f*) is an image picked up along the locus (*e*). (*g*) is an image of difference between (*d*) and (*f*).

In the case of the present invention, as shown in FIGS. 18(*h*) through (*l*), (*i*) and (*k*) are captured in almost the same pick up condition since the locus (*h*) agrees with the locus (*j*). Therefore false defect detection can be prevented. (*h*) through (*l*) in this embodiment of the present invention correspond respectively to (*c*) through (*g*).

Figure 19:
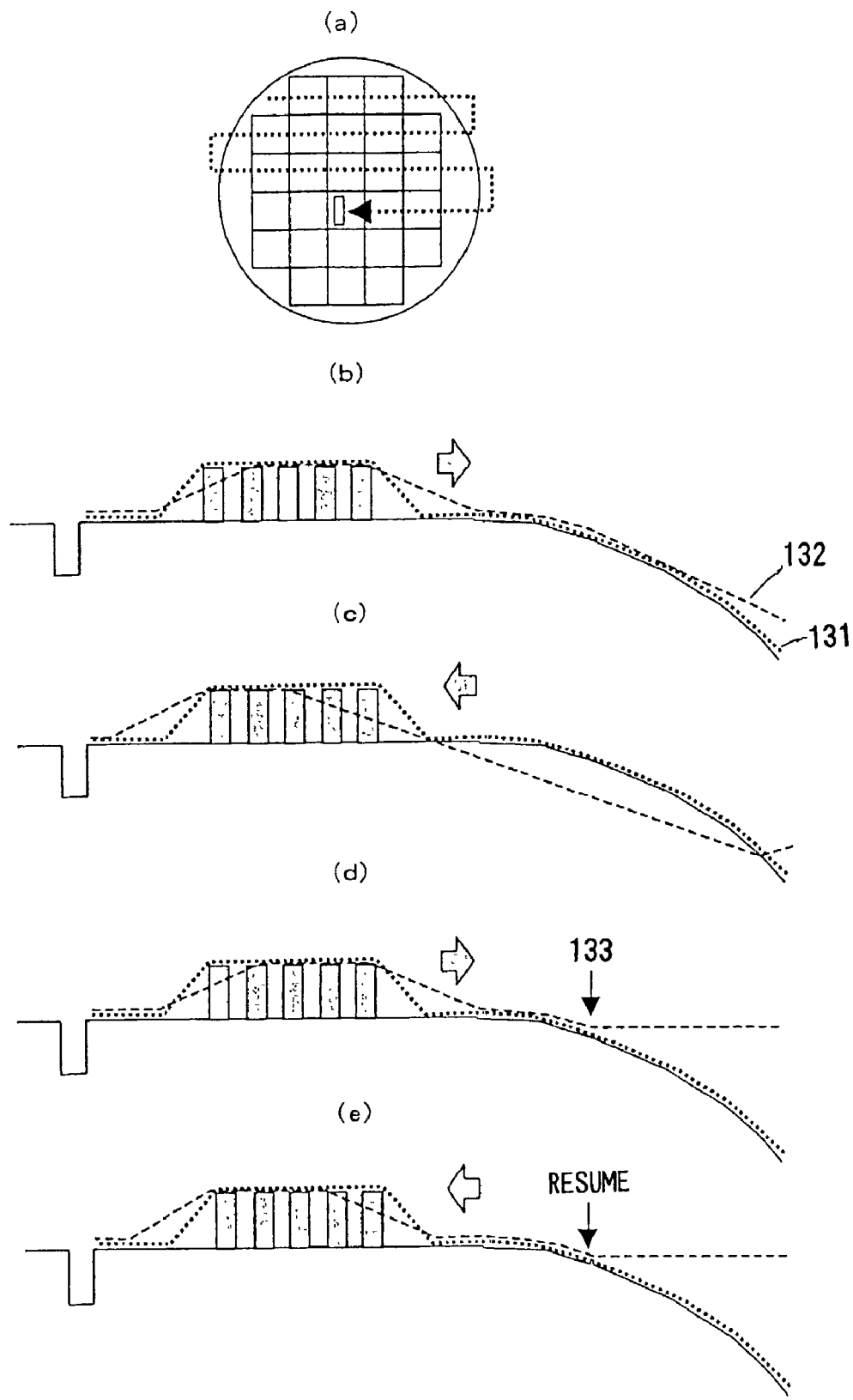
FIG. 19(a) is a top view of a wafer showing how the wafer is scanned where the scanning direction is changed and FIGS. 19(b) through 19(e) show how height detection depends on the scanning direction when a peripheral area is scanned.

Then, using FIG. 19, a description will be made of yet another embodiment of the automatic focus computer 39 according to the present invention. This embodiment intends to secure consistent height detection even after a die's peripheral scribe line is scanned. In such scribe lines, patterns varied greatly in height are formed with a longer exposure shot period than in dies. FIG. 19(*a*) explains what a problem occurs if a scribe line is scanned. Assume that a pattern 510 is formed in a scribe line B509 and not in a scribe line A508. In the scribe line A508, the Z stage 30 rises to track the detected heights 131 and therefore the locus of focal points descends as shown. Therefore, in the up-step area, even if the Z stage 30 ascends at the maximum speed, some distance is required until the locus of focal points 132 is controlled to the pattern surface. Meanwhile, the scribe line B509 results in a different locus of focal points since the pattern 510 is formed there. Thus, if an image detected immediately after the scribe line A is compared with an image detected immediately after the scribe line B, disagreement is likely to occur and cause false defect detection.

Therefore, in this embodiment, stage control is switched on and off by a stage control ON/OFF signal as shown in FIG. 19(b). Based on the current position, the stage control computer 27 sends the control ON/OFF signal 511 to the Z stage 30 via the DIO signal 43. The signal outputs ON (H (High state) in the figure) where image comparison is to be done and OFF (L (Low state) in the figure) where image comparison is not to be done. If stage control is turned off in a scribe line which changes greatly in height, the Z stage does not follow the greatly changing height. Therefore, where image comparison is to be done, the locus 132 of focal points can always be controlled to the pattern surface. Although a scribe line is cited in this embodiment as an example to describe an effect of the present invention, the same effect can be achieved in other cases. For example, stage control may be turned off to prevent errors when the chuck lifts off due to the accelerated/decelerated stage or an area outside the wafer is scanned. This secures the same focal condition where image comparison is to be made.

Methods for preventing pattern steps from inducing errors are described so far. However, the above-mentioned embodiments are described on the assumption that the height detection means 47 can accurately detect the wafer height if no pattern step is involved. As described with FIG. 1, however, errors may also be induced by other wafer surface factors such as the distribution of reflectance and an optically transparent substance.

Thus, the following describes height detection methods according to the prevent invention which can detect the surface height of the sample without being affected by those error factors.

Figure 20:
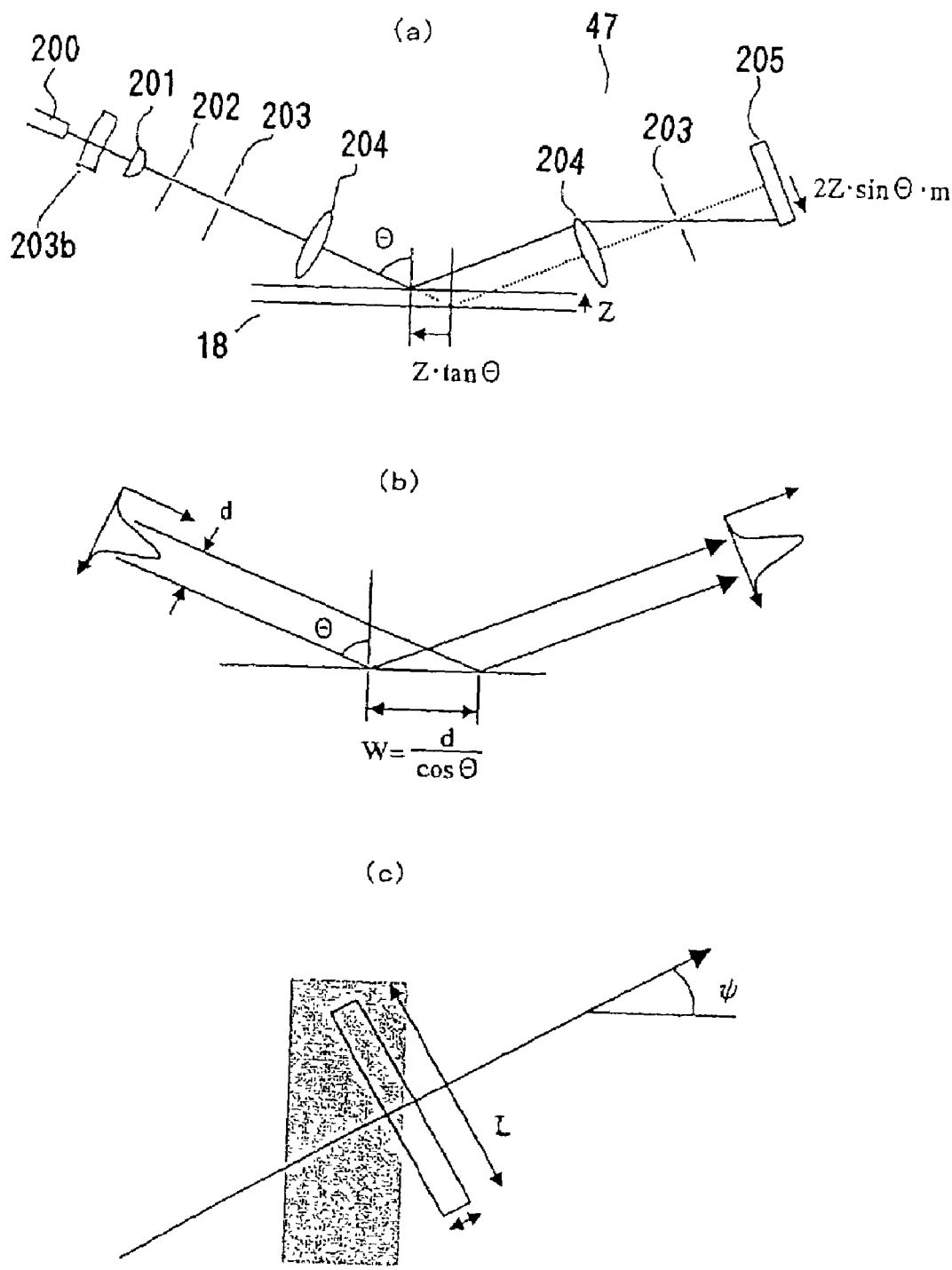
FIGS. 20(a) through (c) are diagrams showing a configuration for a height detection method according to the present invention.

FIG. 20 shows a configuration for a height detection method according to the present invention. An image of a slit 202 is formed on a wafer sample 18 by a slanting light beam which illuminates the sample 18 at an incident angle of $\Theta$. And the slit image on the wafer sample is projected onto an image sensor 205. If the sample moves by Z, the slit image moves by $Z \cdot \tan \Theta$ on the sample and by $2Z \cdot \sin \Theta \cdot m$ on the sensor 205. Where, m is the magnification of the optical system.

$\Theta$ is preferably 80 degrees or larger and more preferably 85 degrees or larger. In the light path, a polarizer 203b is inserted to extract S polarized light. The slit 202 for projection is rotated by $\Psi$ degrees relative to the moving direction of the stage (X). The slit 202 is located at the focus of a condenser lens 201 so that the slit 202 is illuminated uniformly by Koehler illumination. In the illumination path, an iris 203 is located at the back focus of a lens 204 to form a telecentric illumination system so that the size of the slit image does not much change when the sample 18 moves upward or downward.

The diffracted light from the sample 18 may introduce noise to the detected height. A slit 203 is placed at the front focus of the detection lens 204 to remove the diffracted light.

The effectiveness of the above-mentioned configuration will be clarified in the following description. How the above-mentioned configuration is effective to optically transparent substances for the prevention of height detection errors will be described.

FIG. 21 shows how and what error is induced when the height of an optically transparent substance, such as an inter-layer insulation film, is detected. In FIG. 21(a), a slanting incident illumination light beam penetrates or is reflected by a transparent substance. At the top surface of the transparent film, the illuminating light beam divides into reflected light and transmitted light. The transmitted light is reflected at the bottom surface of the transparent film and further divides into transmitted light and reflected light at the top surface. The transmitted light beams are in parallel incident onto the sensor 205. Note that the beams reflected at the bottom are detected at lower portions of the sensor, resulting in the sample's detected position lower apparently than the actual position.

FIG. 21(b) shows the dependence of the reflection of an incident beam upon the incident angle for each polarization. To make the reflectance not smaller than 50%, the incident angle must be 80 degrees or larger in the case of S polarized light 210.

FIG. 21(c) shows the dependence of the height detection error described in FIG. 21(a) upon the incident angle of the illumination beam. Where, the transparent film is 1.0 μm thick and the reflectance is 1.0 at the bottom surface. According to the figure, when S polarized light is used, the incident angle must be not smaller than 85 degrees in order to reduce the height detection error to 200 nm or less, a depth of focus in DUV optical systems. This is because in the configuration described with FIG. 19, the incident angle is set to 80 degrees or more and more preferably to 85 degrees or more and S polarized light is extracted.

Then a description will be made of methods for accurately detecting the surface height of an optically transparent substance without being affected by the distribution of reflectance.

Figure 22:
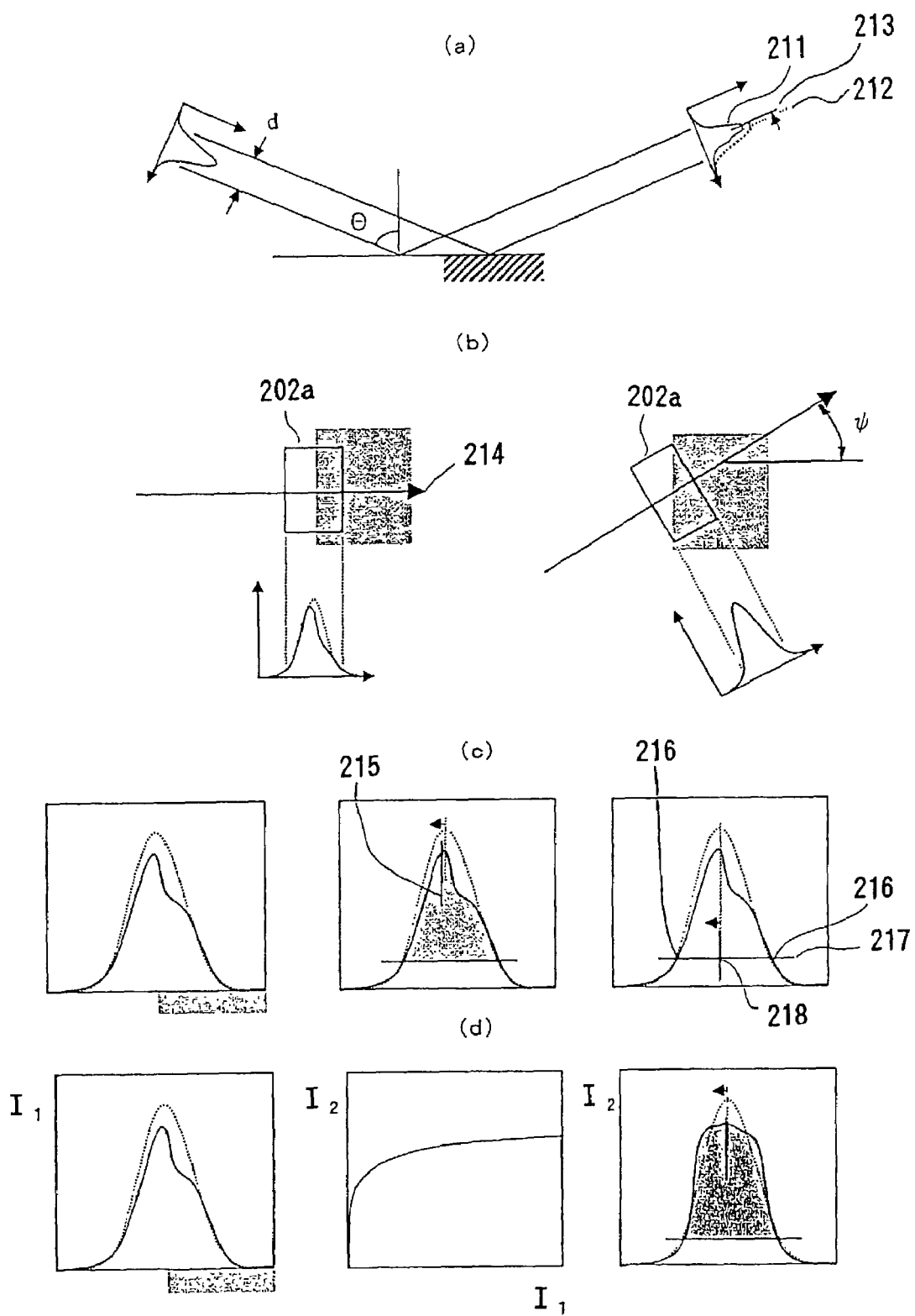
FIG. 22(a) is a sectional view of a sample where a slanting light beam is reflected at an area including a discontinuity of reflectance.
FIG. 22(b) shows a case where projection is made with the slit aligned to the moving direction of the stage (left) and rotated by $\Psi$ degrees with respect to the moving direction of the stage (right).
FIGS. 22(c) and (d) show other error reduction methods.

FIG. 22 shows how an error is induced by the discontinuity of reflectance in the configuration of FIG. 20. In FIG. 22(a), the slit 202 is projected to a region consisting of a low reflectance material on the left side and a high reflectance material on the right side. The distribution of light intensity over the width of the slit results in a distorted distribution shape 211 after reflected from this region. Therefore, an upper position 213 is detected as the position of the slit instead of the position 212 (indicated by a broken linet) which actually corresponds to the slit position. As a result, the apparent detected height is shifted upward than the actual height. FIGS. 22(b) through (d) indicate solutions for reducing this error.

In FIG. 22(b), the slit 202 for projection is rotated by $\Psi$ degrees with respect to the moving direction of the stage. Patterns formed on a wafer are usually parallel or perpendicular to the scanning direction of the stage. In the figure, the slit is projected to a region which crosses two areas differing in reflectance. If the projected slit image 202a is not rotated as shown left, the distribution of light intensity is distorted, resulting in an error. On the other hand, if the projected slit image 202a is rotated as shown right, the distribution of reflectance in the projected region is averaged in the length direction of the slit. In this case, the error is theoretically zero.

FIG. 22(c) shows another solution for reducing the error. Shown left is an example distribution of light intensity after reflected from a region which crosses two areas differing in reflectance. The distribution is distorted and the dented right curve corresponds to the low reflectance area. Shown in the central figure is the result of detecting the slit position by calculating the weighted average of the distribution. In this case, the weighted average 215 is shifted leftward since the remarkably distorted peak. Shown right is an embodiment of the present invention for detecting the position of the slit. Points 216 are the intersections of the predetermined threshold 217 and the distribution curve. The center 218 between the intersections 216 is assumed as the slit position. By setting the threshold to 50% or lower or preferably to about 10% of the maximum value, it is possible to make the detection immune to the influence of the distorted distribution due to the discontinuity of reflectance.

FIG. 22(d) shows yet another embodiment. Shown left is the same as in FIG. 22(c). The central figure plots the following equation (Equation 3):

$$I_2 = \log(I_1 + 1) \quad \text{(Equation 3)}$$

As shown in the figure, a lower level intensity is given a higher gain or a higher level intensity is given a lower gain. As shown right, conversion using this equation compresses the high level portion of the distribution downward, resulting in reducing the influence of the distortion which is remarkable in the high level portion. Needless to say, implementing one of the solutions described in FIGS. 22(b), (c) and (d) or two or all of them at the same time is effective to reducing the error caused by the discontinuity of reflectance.

Then a description will be made of methods for accurately detecting the surface height of an optically transparent substance in step boundaries. In FIG. 24, an illumination beam is irradiated to step boundaries in the configuration of FIG. 20. First, FIG. 24(b) shows how an error is induced at a down-step boundary (221). As shown, the slit beam is moving from the upper surface to the lower surface. In the left figure, the upper surface is illuminated. Although the position (223) indicated by a broken line corresponds to the upper surface to be detected, the illumination beam divides into two beams due to the boundary before reaching the sensor 205. The beam (223) reflected at the lower surface has a smaller amount of light than the beam (224) reflected at the upper surface and therefore is detected with lower contrast. Due to this, the height is detected based on the beam from the upper surface, resulting in an apparent detected height (225) shifted upward. In the right figure where the slit beam has moved rightward, the apparent detected height is shifted downward since the beam (226) reflected at the lower surface is detected. This is because the resulting locus (227) of detected heights shown in FIG. 24(a) includes heights which actually do not exist.

Then, FIG. 24(c) shows how an error is induced at a up-step boundary (229). As shown, the slit beam is moving from the lower surface to the upper surface. In the left figure, the lower surface is illuminated. As shown, only the beam reflected at the upper surface is detected since the beam from the lower surface is shielded. Therefore, the apparent detected height is shifted upward. Also in the right figure where the slit beam has moved rightward, the apparent detected height is shifted downward since only the beam reflected from the upper surface is detected. This is because the resulting locus (228) of detected heights shown in FIG. 24(a) includes heights which actually do not exist.

Figure 25:
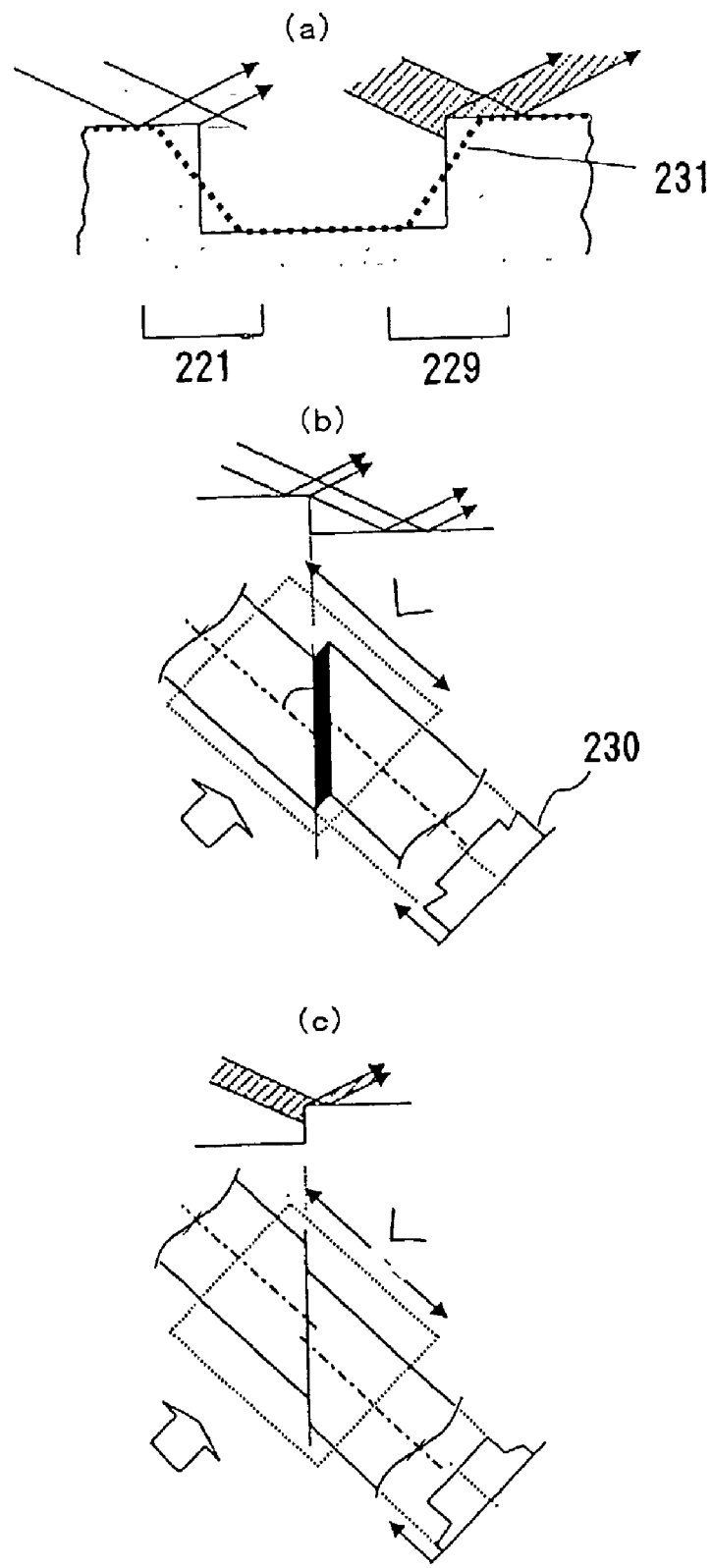
FIGS. 25(a) through (c) shows a method for reducing the height detection error at a step boundary by rotating the slit by some angles with respect to the direction of the step boundary.

Then, referring to FIG. 25, a description will be made of an embodiment of the present invention for reducing the error induced by steps. According to the present invention, the illuminated slit 202 is rotated by Ψ degrees with respect to the direction of the current step as shown in FIG. 20(c) and slit light is integrated over the range L in the length direction of the slit as shown in FIG. 25(b). Although the slit light is divided at the down-step (221) in FIG. 25(b), the detected distribution (230) is continuous not like in FIG. 24(b). Similarly, although the slit beam is partially blocked by the up-step in FIG. 25(c), the apparent shift of the slit beam due to the block can be reduced since the integration range L includes an unblocked region. A broken line in FIG. 25(a) is the locus of heights detected in step boundary areas in this embodiment. The detected values (231) converge to the average height of the sample between the upper surface height and the lower surface height according as the integral range L gets longer. With FIGS. 21 through 25, the effectiveness of the configuration of FIG. 20 has so far been described.

Then, referring to FIG. 26, a description will be made of a first embodiment of the present invention for detecting the heights of several points (45a through 45i) around the image pickup area 44 shown in FIG. 5. This embodiment shown in FIG. 26(a) has the same configuration as that shown in FIG. 20 and is characterized in that a divided sensor (232) is employed as the photosensitive sensor in FIG. 20(a). FIG. 26(a) is a side view of the embodiment while FIG. 26(b) is a top view of the embodiment. FIG. 26(c) shows the relations between the image pickup position of the linear sensor (44) and the height detecting positions in this embodiment applied to the configuration of FIG. 2. FIGS. 26(d) through (f) concern an implementation of the divided sensor (232). Common coordinate systems (XYZ for the sample surface and Y'Z' for the sensor surface) are used in FIGS. 26(a) through (f). In FIG. 26(d), a line of PSDs in the Y' direction is viewed from the sample surface toward the sensor surface. By calculating how much the slit is shifted in the Z' direction at the respective Y' positions, the heights of the sample's surface at its corresponding points can be detected. Positive shift of the slit in the Z' direction means that the sample is lowered in the Z direction. PSDs A through E correspond to detection points A through E of FIG. 26(c). The layout of FIG. 26(c) is an implementation of FIG. 5 and allows detection at plural points spaced at equal intervals around the image pickup area 44 both in the stage's scan direction 46 and the length direction of the image pickup area 44. Accordingly, the height detecting methods described respectively with FIGS. 8 through 10 can be realized by making the automatic focus computer 39 calculate maximum and minimum values from the heights detected by A through E in FIG. 26(c). A divided sensor used to obtain the result of FIG. 26(e) comprises a line of two-part photodiodes arranged in the Y' direction and provides the same function as the PSDs in FIG. 26(d). A divided sensor used for FIG. 26(f) is a two-dimensional CCD sensor. By calculating the shift of the slit in the Z' direction at each pixel position in the Y' direction, the height distribution of the sample surface can be detected in detail. In addition, this CCD sensor allows the distribution processing methods of FIGS. 22(c) and (d) to be implemented for the detected slit light distribution in the Z' direction.

Then, referring to FIG. 27, a description will be made of a second embodiment of the present invention for detecting the heights of plural points (45a through 45i) around the image pickup area 44 shown in FIG. 5. This embodiment is based on the configuration of FIG. 20 and is characterized in that a fast one-dimensional sensor is used to implement such distribution processing for plural points as by a two-dimensional CCD sensor in FIG. 26(f) and additional features are inserted in the detection light path. FIG. 27(a) is a side view of the embodiment while FIG. 27(b) is a top view of the embodiment. The reflected beam from the sample 18 is enlarged and detected by a detection lens 204. An iris 203 is located at the back focus of the detection lens 204 to block scattered light from the sample 18. A cylindrical lens 233 serves to collimate the detected beam since it located in such a manner that its front focus falls on the back focus of the detection lens 204. The collimated beam is shifted by parallel-shifting prisms 234 which are rotated with respect to the length direction of the slit. FIG. 27(d) shows the principle of the parallel-shifting prism 234. A light beam entering a parallel glass at an incident angle of $\Theta$ is shifted by the distance $\delta$ given by the following equation (Equation 6):

$$\delta = (1 - 1/N \cdot \cos \Theta / \cos \Theta') d \cdot \sin \Theta \qquad \text{(Equation 6)}$$

Where, N is the refractive index of the glass, d is the thickness of the glass and $\Theta'$ is the angle of the diffracted beam with respect to the normal of the incident plane. In FIG. 27(a), three parallel-shift prisms 234 associated respectively with the central, right and left portions of the length of the slit are used to shift the right and left portions of the slit beam in parallel. A one-dimensional line sensor is located at the back focus of the cylindrical lens 235. The three branches of the slit beam are focused on distant pixels of the one-dimensional line sensor. FIG. 27(c) shows the relations between the image pickup position of the linear sensor (44) and the height detecting positions in this embodiment applied to the configuration of FIGS. 2. A, B and C in FIG. 27(c) correspond to A, B and C in FIG. 27(e) where the slit light distribution detected by the line sensor 236 is shown. When the distribution shifts positively in the Z' direction, this means that the sample surface has become lower. By calculating the amplitudes of A, B and C with respect to the origin, it is possible to determine how high the sample is at the respective detection points. The layout of FIG. 27(c) is an example implementation of FIG. 5 and allows detection at plural points spaced at equal intervals around the image pickup area 44 both in the stage's scan direction 46 and the length direction of the image pickup area 44. Accordingly, the height detecting methods described respectively with FIGS. 8 through 10 can be realized by making the automatic focus computer 39 compare and calculate the detected heights A, B and C shown in FIG. 27(c).

Figure 26:
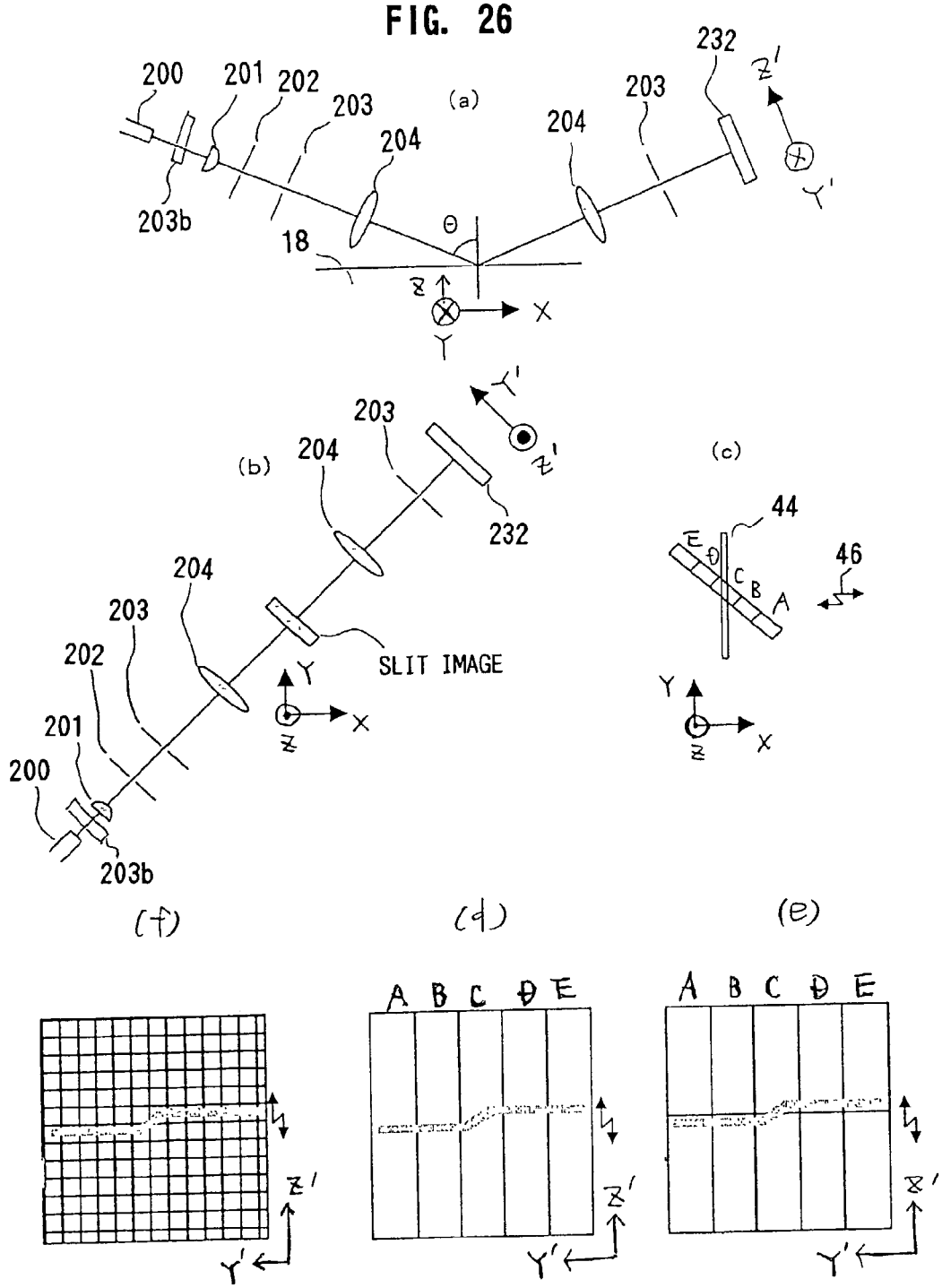
FIG. 26(a) concerns a first embodiment of the present invention for detecting the height of the sample at plural positions. This configuration is the same as the configuration of FIG. 20(a) except in that a divided sensor is used for the photosensitive sensor.
FIG. 26(b) is a top view of the configuration FIG. 26(a).
FIG. 26(c) shows the relations between the image pickup position of the linear sensor and the height detecting positions in this embodiment applied to the configuration of FIG. 2.
FIGS. 26(d) through (f) show example implementations of the divided sensor.
Figure 27:
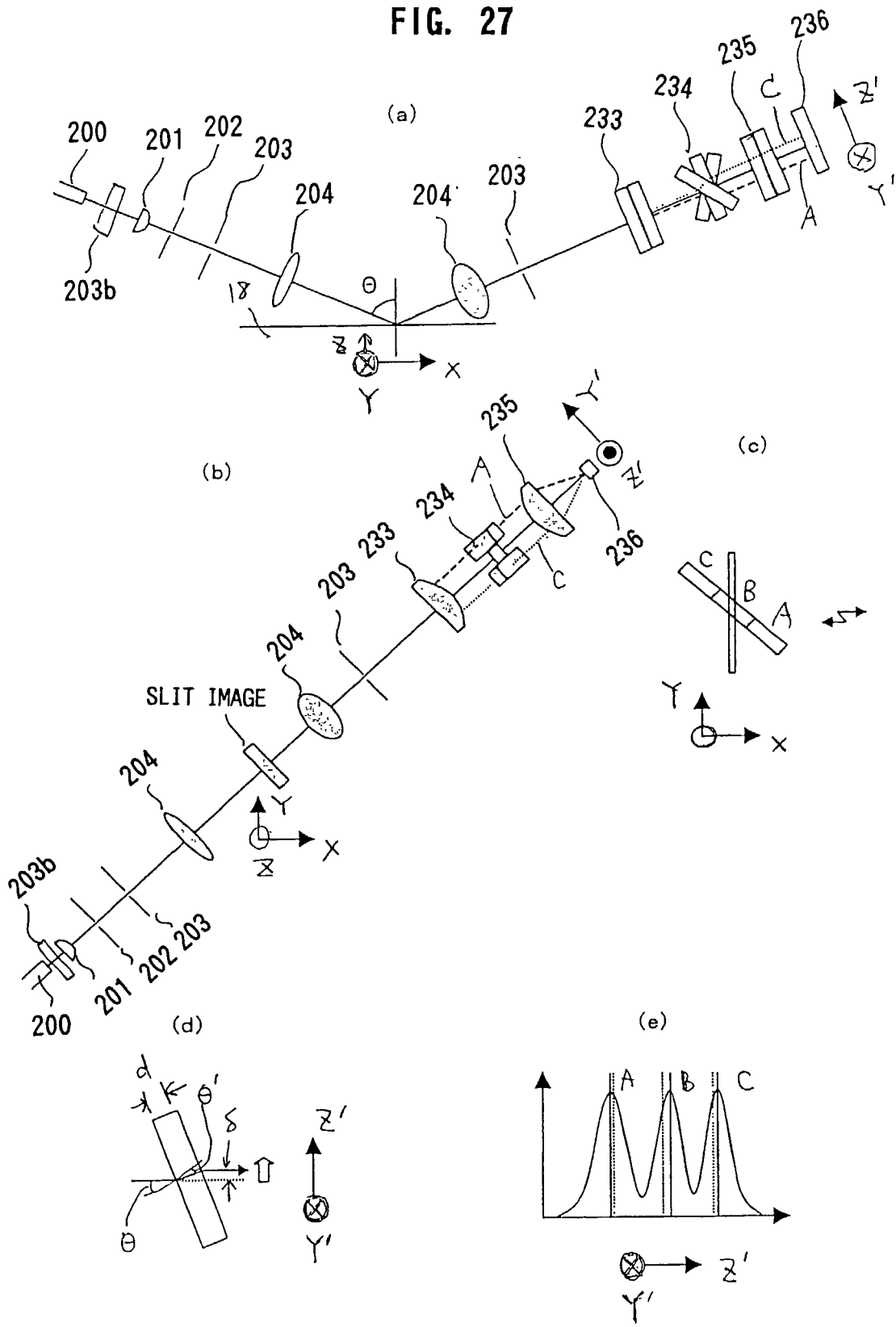
FIG. 27(a) concerns a second embodiment of the present invention for detecting the height of the sample at plural positions. This configuration is the same as the configuration of FIG. 20(a) except in that a one-dimensional sensor is used for the photosensitive sensor.
FIG. 27(b) is a top view of the configuration FIG. 27(a).
FIG. 27(c) shows the relations between the image pickup position of the linear sensor and the height detecting positions in this embodiment applied to the configuration of FIG. 2.
FIGS. 27(d) through (e) show example implementations of the one-dimensional sensor.
Figure 28:
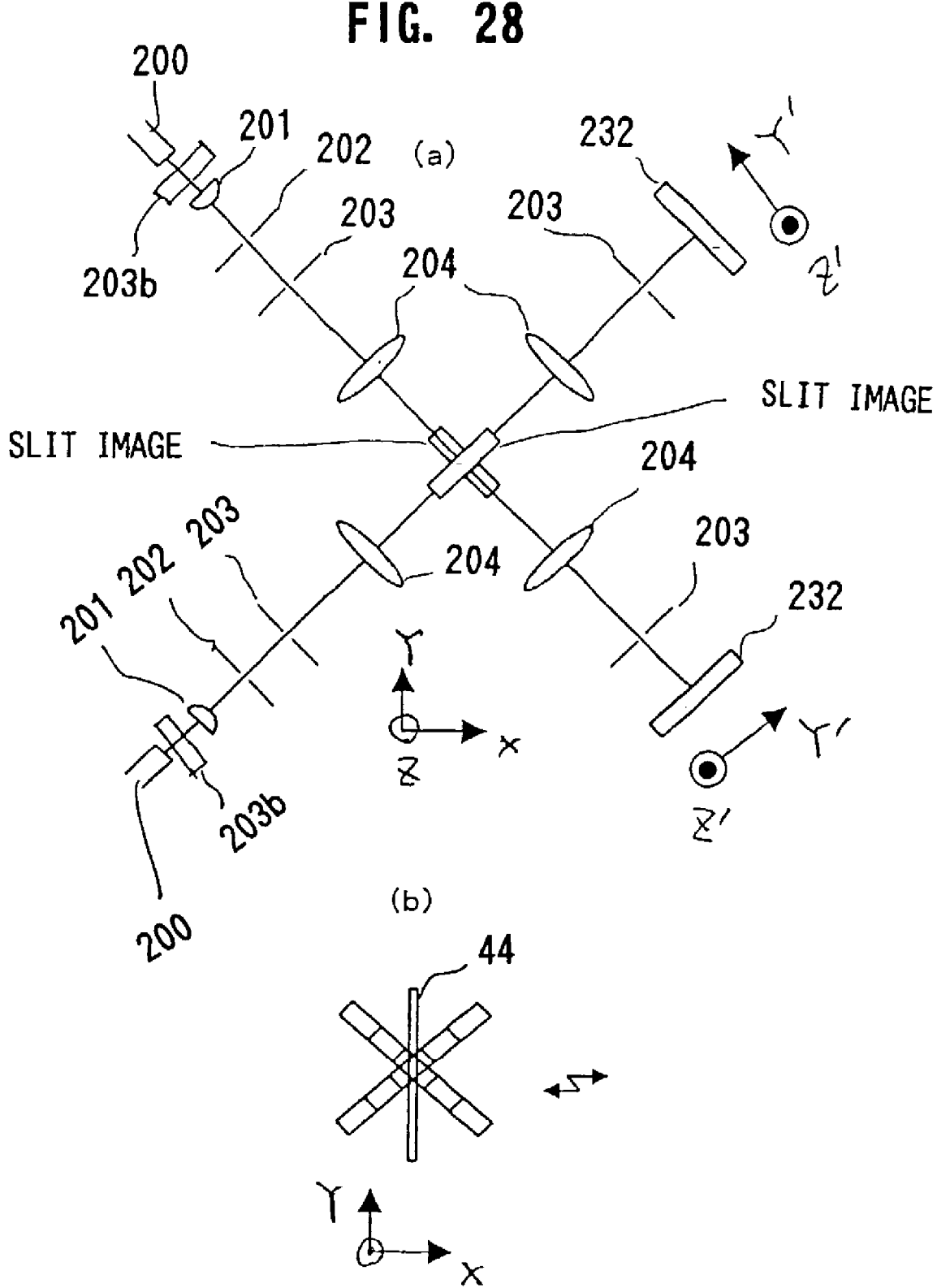
FIGS. 28(a) and (b) are diagrams of dual configuration of the height detection means shown in FIG. 26.

In FIG. 28, the configuration of FIG. 26 is dually implemented. FIG. 28(a) is its top view and FIG. 28(b) shows the relations between the image pickup position of the linear sensor (44) and the height detecting positions in this embodiment applied to the configuration of FIG. 2. The layout of FIG. 28(b) is an example implementation of FIG. 5. As compared with the layout of FIG. 26(c) with one direction, this layout is characterized in that accurate height detection is possible regardless of whether the sample has steps and patterns which are not symmetrical in the length direction of the linear sensor.

Methods for accurately detecting the surface heights of a wafer involving steep pattern steps, discontinuous reflectance distributions, optically transparent substances, etc. have been described so far with FIGS. 20 through 28.

The configuration of FIG. 20 is height detection means and its light path is independent of that of the image pickup optical system. Therefore, it is necessary to eliminate the drift of the origin from the focal point of the image pickup optical system. The origin must be stable against the change of the environment, especially the change of temperature. FIG. 29 explains the drift of the origin. FIG. 29(a) shows an example implementation of integrating the height detecting optical system of FIG. 20 into the configuration of FIG. 2. The beam from a slit 205 is focused on the sample position by two achromat lenses 291. The reflected beam is focused intermediately by two achromat lenses 291 and enlarged by an objective lens 200 for securing sensitivity. The illuminating light source and the subsequent light path after the objective lens 200 are omitted from the figure. Shown in the figure is the area sensitive to the environmental change. Each component of the height detecting optical system 47 is fixed to a base structure 295. Shown in FIG. 29(a) is the initial state of the height detecting optical system 47. In FIG. 29(b), the lens-barrel 296 of the objective lens 17 and the base structure 295 of the height detecting optical system are thermally expanded. In FIG. 29(c), the top end portion of the objective lens 17 is shown in detail. Although the focal point of the height detecting optical system initially agrees with that of the image pickup optical system, they respectively moved to different points due to the rise of temperature. Therefore, since the focal point of the image pickup system relative to the origin of the height detecting system changes, it is no longer possible to use automatic focusing offset values (recipes) registered to the defect detection apparatus.

The following describes a calibration method for compensating for such an influence of environmental changes. This method makes it possible to use past recipes regardless of environmental changes and share recipes with other apparatuses.

Referring to FIG. 30, the calibration method will be described. In this calibration, two different standard samples 453 and 454 are mounted on the wafer chuck 23 of FIG. 2. One sample 453 is a mirror on which no pattern is formed and used for shading correction. The other sample 454 has a micro-pattern formed thereon and is used in the calibrating procedure described in FIG. 30. The calibration is performed before inspection and during inspection if the temperature detected by the temperature monitor installed in the apparatus exceeds a pre-determined threshold. It is also preferable to periodically perform the calibration. FIG. 30(a) is a flowchart of the calibration. First, the X and Y stages 25 and 26 are moved to align the standard sample 453 to the optical axis (S31). Then, the standard sample 454 is moved into the auto-focus range (S32). This step is shown in detail in FIG. 30(b). First, the Z stage is moved to its lowest position (S321) and moved upward in steps of a pre-determined amount (S322). According to whether a light beam is incident on a photosensitive sensor, the automatic focus computer 39 judges whether the sample is in the detection range (S323). If not, the operation goes back to step S322. If the sample is judged to be in the detection range, the AF is turned on (S324) to proceed with the next step of (a)(S33). After the Z stage is moved by a certain amount (S33), height detection is made by the automatic focus computer 39 (S34) and the detection result is sent to the general control unit 9. Then, an image is detected by a TV camera 21 (S35) and a contrast value is calculated in the image-processing unit 22 from the detected image (S36). The contrast value is a kind of dispersion in a specific area of the image. These steps are repeated a specified number of times (S36) to make the image-processing unit 22 or the general control unit 9 obtain a curve shown in FIG. 30(c). The horizontal axis represents the height of the sample while the vertical axis represents the contrast value. By interpolating this curve by a polynomial, for example, a quadric, its peak position (best focus position) Zo is determined (S37). The Zo is recorded in the automatic focus computer as a calibration offset (S38).

Figure 31:
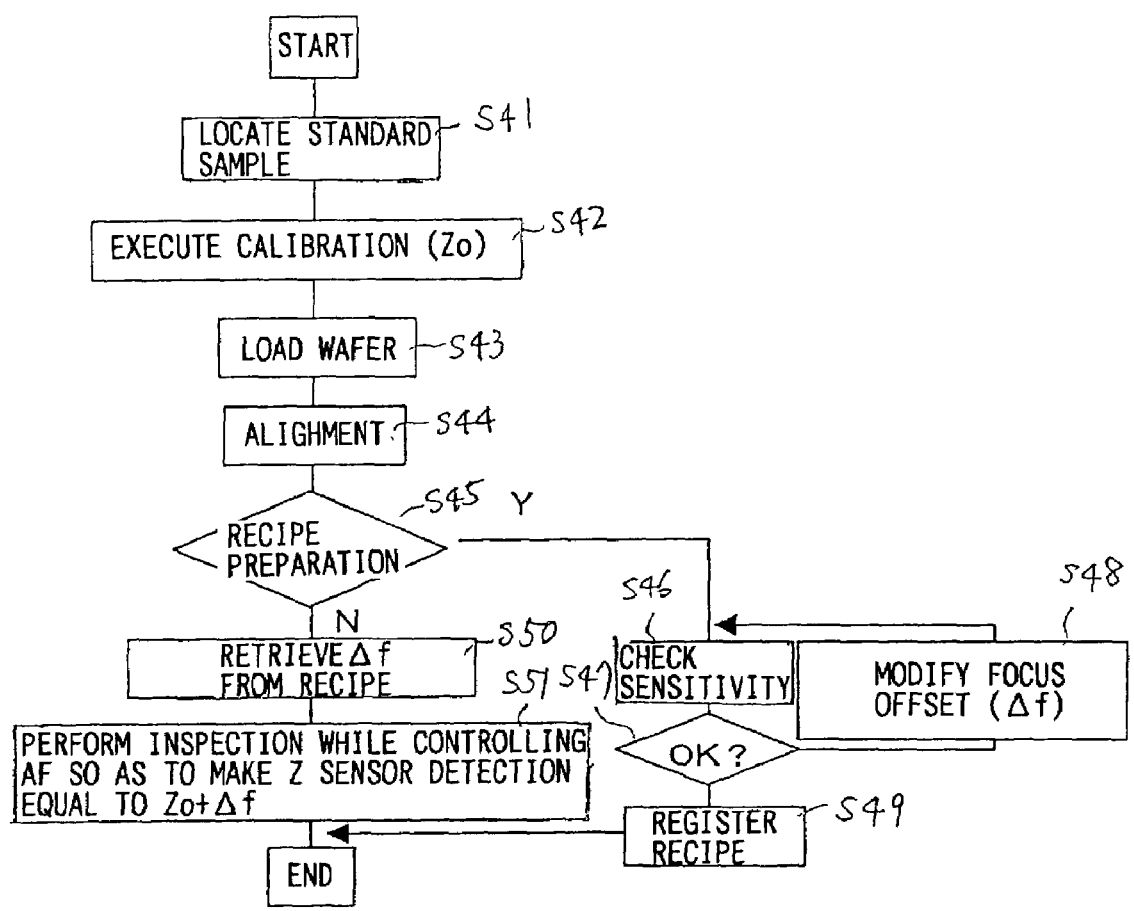
FIG. 31 is a flowchart showing how to use the calibration offset.

Then a method of using the recorded calibration offset will be described with reference to FIG. 31. Before inspection is started, the standard sample 454 is located (S41) and the calibration offset Zo is determined as described in FIG. 30 (S42). Then, a wafer is loaded (S43) and alignment is performed (S44). In the case of automatic inspection, the focus offset $\Delta f$ is read out from the recipe (S50) and inspection is performed while controlling the Z stage 30 so as to make the detected height equal to Zo+$\Delta f$ (S51). If a recipe is to be prepared (S45), the inspection sensitivity is checked (S46) and, if not OK (S47), the focus offset $\Delta f$ is modified so as to optimize the inspection sensitivity (S48) before the recipe is registered (S49).

In a short term, the above-mentioned calibration is effective for the drift of the origin. To secure the throughput, however, it is necessary to reduce the calibration frequency by structurally reducing the drift of the origin.

FIG. 32 explains the amount of drift in the height detecting optical system. In the figure, the base structure 295 and the shoulder 450 of the objective lens 17 are fixed to the same plane. In this configuration, the shift of the top mirrors 451 can be considered as the amount of drift.

FIG. 32(a) explains what influence occurs when the supporting structure of the height detecting optical system expands thermally in the horizontal direction. The amount of horizontal thermal expansion at $\Delta T°$ C. is given by the following equation (Equation 7):

$$\Delta R = \alpha \cdot R \cdot \Delta T \quad \text{(Equation 7)}$$

Where, $\alpha$ is the thermal expansion coefficient of the base structure 295 and R is the distance from the focal point to the top mirror 451 in the height detecting optical system.

Then, the height change $\Delta Z_H$ due to $\Delta R$ is given by the following equation (Equation 8):

$$\Delta Z_H = \alpha \cdot R \cdot \Delta T / \tan \Theta \quad \text{(Equation 8)}$$

Where, $\Theta$ is the incident angle of the illuminating light beam.

FIG. 32(b) explains what influence occurs when the supporting structure of the height detecting optical system expands thermally in the vertical direction. The height change $\Delta Z_V$ at $\Delta T°$ C. is given by the following equation (Equation 9):

$$\Delta Z_v = \alpha \cdot H \cdot \Delta T \quad \text{(Equation 9)}$$

Where, H is the distance from the base fixed position to the top mirror.

Figure 33:
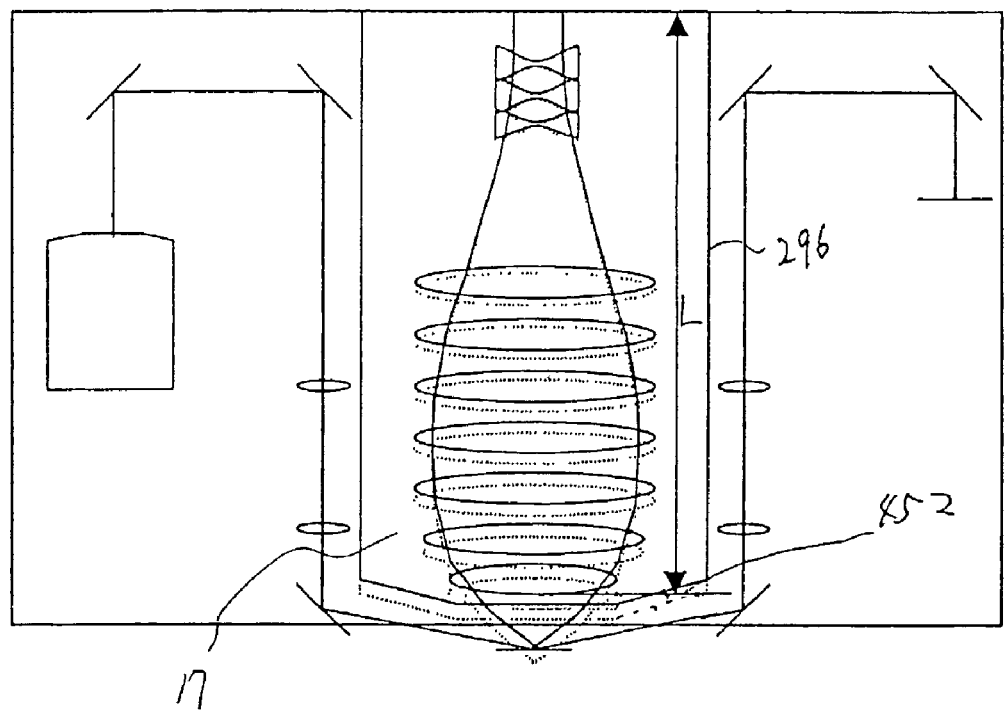
FIG. 33 is a diagram for explaining the amount of drift of the objective lens.

FIG. 33 explains the drift of the objective lens 17. The lens group of the objective lens 17 is held by the lens top 452. Therefore, the drift of the objective lens 17 may be attributable to the expansion and contraction of the lens barrel 296 (up to its lens top) and the change of the optical system's focal length. Therefore, the objective lens's drift $\Delta Z_O$ is given by the following equation (Equation 10):

$$\Delta Z_O = (\beta \cdot L + \gamma) \cdot \Delta T \quad \text{(Equation 10)}$$

Where, $\beta$ is the thermal expansion coefficient of the barrel 296 of the objective lens, L is the distance from the shoulder of the objective lens to its lens top and $\gamma$ is the thermal change rate of the distance from the lens top to the focal point in the optical system. $\gamma$ can be determined by optical simulation.

As implied above, the amount of drift can be minimized if $\Delta Z_O = \Delta Z_H + \Delta Z_V$ is met. Substituting (Equation 8), (Equation 9) and (Equation 10) into $\Delta Z_O = \Delta Z_H + \Delta Z_V$ results in the following equation (Equation 11):

$$H = (\beta \cdot L + \gamma - \alpha \cdot R / \tan \Theta) / \alpha \quad \text{(Equation 11)}$$

That is, H must be designed to be equal to the value of the right side of (Equation 11).

Figure 34:
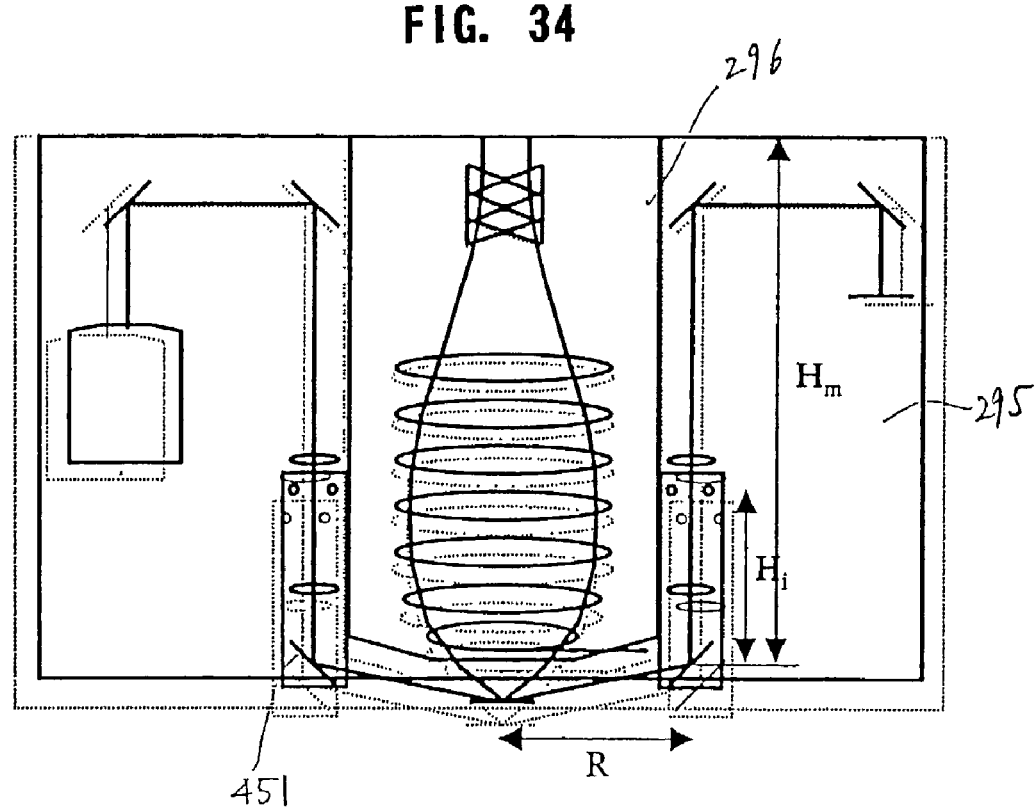
FIG. 34 shows a configuration for adjusting the position of the top mirror.

Then, referring to FIG. 34, a description will be made of an example implementation of the configuration which allows H to be adjusted to the value of the right side of (Equation 11). The base structure 295 has a larger thermal expansion coefficient than the barrel 296 of the objective lens. Accordingly, the base support 295 may be made of, for example, aluminum ($\alpha = 23$) if the barrel 296 is made of brass ($\beta = 17.5$). The component for mounting the top mirror 451 is made of a material whose thermal expansion is enough small to be negligible, for example, Super Invar. With these materials selected, it is possible to reduce the amount of drift by setting H (distance up to the position where the top mirror mounting component) equal to the right side of (Equation 11).

The image pickup apparatus and the defect detection apparatus which are capable of high resolution detection of the surface condition of a wafer, not depending on the surface condition have been described so far.

Then, with reference to FIG. 35, a description will be made of defect detection results obtained by using the defect detection apparatus described above.

In prior art, as shown in FIG. 35(a), defocus occurs where a transparent film is formed, a pattern step exists and reflectance changes. As shown in FIG. 35(b), this may result in unnecessarily detected defects such as 499 on a layer under an inter-layer film and overlooked defects in pattern step boundaries and reflectance discontinuity boundaries. Meanwhile, according to present invention, pattern surface images can be detected reliably as shown in FIG. 35(c) and therefore the defect 499 on the lower layer is not detected and defects overlooked in FIG. 35(b) can be detected.

Then, with reference to FIG. 36, a description will be made of an example method for discriminating lower layer defects from surface defects if such lower layer defects are detected. Although according to the present invention, images can be picked up for defect detection with a very narrow depth to focus set to the pattern surface, a very large defect on the lower layer and a defect just below the surface may be detected by compare inspection. However, since these defects are defocused as shown in FIG. 36(b), they can be distinguished from surface defects based on the characteristics of their images. Shown in FIG. 36(c) is a result of differentiating FIG. 36(b). The defocused lower layer defect 499 has low differential values due to the dimmed contour while a surface defect 498 has high differential values due to the clearly captured contour. FIG. 36(d) shows a sectional view of the differentiated image (c). For example, the feature extraction circuit of FIG. 4 can be used to calculate the maximum-to-minimum difference of the differential value for each defect in FIG. 36(d) and output it as defect information for discrimination of lower layer defects from surface defects.

With reference to FIG. 37, the following describes an example implementation of a review screen. Although a scanning image pickup system using a linear sensor is assumed in the above description, the present invention can also be applied to an image detection system using a TV camera such as a CCD image sensor. FIG. 37(a) is a diagram for explaining the defect review screen. In the figure, Automatic Focus Set 304a is selected for the review and Average is selected as Height Calculation Rule 304ab. As a result, a defect 500 can not be recognized clearly due to the defocused pattern step image. Meanwhile, the pattern image and the defect 500 can be clearly observed in FIG. 37(b) where Max is selected as Height Calculation Rule 304ab to focus the pattern step surface.

As described so far, the present invention provides a method for selectively detecting defects introduced by a specific process of concern by using a high resolution and narrow depth of focus image pickup optical system. In FIG. 2, an implementation of a high resolution and narrow depth of focus image pickup optical system using a DUV light source is shown. The same object can also be achieved by using a confocal microscope for the image pickup system in the configuration. In addition to optical image pickup systems cited so far in the description of embodiments, the present invention is also applicable to scanning electron microscopes and electron beam pattern defect detection apparatuses.

The present invention makes it possible to capture high resolution images of the surface condition of a circuit pattern-formed wafer without being affected by steep pattern steps caused after resist patterns are formed and etched, discontinuous reflectance distributions and optically transparent substances. Defect detection based on the images realizes high sensitivity defect detection.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

The invention claimed is:

1. An image detection method comprising the steps of:
sequentially picking up a surface image of a sample at an image pickup position by using image pickup means while moving a scanning stage in one direction and said stage having the sample mounted thereon;
sequentially detecting a surface height of the sample at plural points including two points which are respectively on the opposite sides of the image pickup position in said one direction by projecting a slit-shaped light onto a region stretching over said image pickup position, dividing an image of said slit-shaped light projected on said position into plural images and detecting said divided plural images with a linear image sensor while sequentially picking up a surface image of the sample at the image pickup position;
sequentially Calculating the height of the sample at the image pickup position based on the height information detected sequentially at the plural points;
adjusting the focal position of the image pickup means by using the sample height information sequentially calculated for the plural points; and
sequentially picking up a surface image of the sample at the image pickup position by using the image pickup means whose focal position is adjusted while moving the scanning stage having the sample mounted thereon.

2. An image detection method according to claim 1 wherein the height detection is done at the plural points in synchronization with the scanning stage.

3. An image detection apparatus comprising:
a scanning stage movable in one direction and said stage having a Sample mounted thereon;
an image pickup system which sequentially picks up a surface image of the sample at an image pickup position by moving the scanning stage;
a height detection unit which sequentially detects the surface height information of the sample at plural points including two points which are respectively on the opposite sides of the image pickup position in said one direction by projecting a slit-shaped light onto a region stretching over said image pickup position, dividing an image of said slit-shaped light projected on said position into plural images and detecting said divided plural images with a linear image sensor while the image pickup system sequentially picks up a surface image of the sample at the image pickup position;
a sample height calculation unit which sequentially calculates a height of the sample at the image pickup position based on the height information detected sequentially at the plural points by the height detection unit; and
a focus control unit which focuses the image pickup system by using the sample height calculated sequentially by the sample height calculation unit.

4. An image detection apparatus according to claim 3 wherein the height detection unit executes an operation to detect the height of a sample or an object to be inspected in synchronization with a positional signal concerning the scanning stage.

5. A defect detection method comprising the steps of:
sequentially detecting surface height information of an object to be inspected at plural points including two points which are respectively on the opposite sides of an image pickup position in the scanning direction by projecting a slit-shaped light onto a region stretching over said image pickup position, dividing an image of said slit-shaped light projected on said position into plural images and detecting said divided plural images with a linear image sensor while moving a scanning stage having the object mounted thereon;
sequentially calculating a height of the object at the image pickup position based on the height information detected sequentially at the plural points;
focusing the image pickup means by using the object height data calculated sequentially;
picking up a surface image of the object at the image pickup position by using the focused image pickup means while moving the scanning stage having the object mounted thereon;
comparing the picked up image with a standard reference image and detecting defect candidates;
picking out a real defect from the detected defect candidates;
extracting a feature amount from the real defect picked out; and
outputting the extracted feature amount information about the real defects.

6. A defect detection method according to claim 5 wherein the object height detection is executed in synchronization with a positional signal concerning the stage.

7. A defect detection method comprising the steps of:
picking up a surface image of an object to be inspected by using image pickup means while moving a scanning stage in one direction and said stage having the object mounted thereon;
comparing the picked up image with a standard reference image and detecting defect candidates;
picking out a real defect from the detected defect candidates;
extracting a feature amount from the real defect picked out; and
outputting the extracted feature amount information about the real defect,
wherein the object comprises a plurality of pattern-formed layers and when a surface image of the object is picked up, the focus of the image pickup means is adjusted in such a manner that the uppermost layer pattern of the object mounted on the scanning stage is in focus and the lower layer pattern of the uppermost layer is out of focus by projecting a slit-shaped light onto a region of said object stretching over an image pickup position picked up by said image pickup means from an angle over 80 degrees from normal, dividing an image of said slit-shaped light projected on said position into plural images and detecting said divided plural images with a linear image sensor.

8. A defect detection method according to claim 7 wherein the focus adjustment is done based on the height data measured at a plurality of surface points of the object around the area to be picked up by the image pickup means.

9. A defect detection method comprising the steps of:
picking up an image of an object to be inspected, which has plural pattern layers formed thereon, in such a manner that a single layer pattern is in focus and the other layer patterns are out of focus by projecting a slit-shaped light onto a region of said object stretching over an image pickup position picked up by said image pickup means from an angle over 80 degrees from normal, dividing an image of said slit-shaped light projected on said position into plural images and detecting said divided plural images with a linear image sensor;
comparing the picked up image, where said single layer pattern is in focus, with a standard reference image to detect defect candidates; and
picking out a real defect on said single layer pattern from the detected defect candidates.

10. A defect detection method according to claim 9 wherein said single layer pattern of the plural layer patterns is the uppermost layer pattern of the plural layer patterns.

11. A defect detection method according to claim 9 wherein the object to be inspected is irradiated with DUV light.

12. A defect detection method according to claim 9 wherein a TDI sensor is used to pick up an image of the object to be inspected.

13. A defect detection method according to claim 9, further comprising the steps of:
extracting a feature amount from the real defect picked out; and
outputting feature amount information about the real defect picked out.

14. A defect detection method comprising the steps of:
detecting the surface height of an object to be inspected, which has plural pattern layers formed thereon, while moving a scanning stage having the object mounted thereon by projecting a slit-shaped light onto a region stretching over said image pickup position, dividing an image of said slit-shaped light projected on said position into plural images and detecting said divided plural images with a linear image sensor;
adjusting the relation between the focus of image pickup means to pick up an image of the object and the surface height of the object based on the detected surface height of the object;
picking up a pattern image of the object by using the image pick means with the relation between the focus of the image pickup means and the surface height of the object adjusted;
comparing the picked up image with a recorded reference image to detect defect candidates; and
picking out a real defect from the defect candidates picked out,
wherein, the pattern image Pickup step is done in such a manner that the lower layer patterns below the uppermost layer pattern are out of focus.

15. A defect detection method according to claim 14 wherein the surface height of the object to be inspected is detected by an optical system different from the image pickup system.

16. A defect detection method according to claim 14 wherein the object to be inspected is irradiated with DUV light.

17. A defect detection method according to claim 14 wherein a TDI sensor is used to pick up an image of the object to be inspected.

18. A defect detection method according to claim 14, further comprising the steps of:
extracting a feature amount from the real defect picked out; and
outputting feature amount information about the real defect picked out.

19. A defect detection apparatus comprising:
a stage on which an object to be inspected is mounted;
illumination means for illuminating the object mounted on the stage;
a recording unit for recording height information on the object illuminated by the illumination means in association with the coordinates of each corresponding position;
an image pickup system which obtains a surface image of the object by sequentially picking up an optical surface image of the object at an image pickup position while moving the stage;
an object height calculation unit which sequentially calculates the height of the object at the image pickup position by using the height information recorded in the recording unit while a surface image of the object is sequentially picked up at the image pickup position by projecting a slit-shaped light onto a region stretching over said image pickup position, dividing an image of said slit-shaped light projected on said position into plural images and detecting said divided plural images with a linear image sensor;
a focus control unit which focuses the image pickup system by using the object height information calculated sequentially by the object height calculation unit; and
an image processing unit which compares an image obtained from the image Pickup system with a standard reference image to detect a defect or defect candidates.

20. A defect detection apparatus according to claim 19 wherein the height information recorded in the recording unit is a focus map.

21. A defect detection apparatus according to claim 19 wherein the illumination means uses DUV light to illuminate the object.

22. A defect detection apparatus according to claim 19 wherein the image pickup system is provided with a TDI sensor and a surface image of the object is obtained by detecting an optical surface image of the object with the TDI sensor.

23. A defect detection apparatus according to claim 19 wherein the control unit controls the height of the stage by using the object height information calculated sequentially by the calculation unit.

24. A defect detection apparatus comprising:
a stage on which an object to be inspected is mounted;
illumination means for illuminating the object mounted on the stage;
an image pickup system which obtains a detected image signal by sequentially picking up an surface image of the object illuminated with the illumination means at an image pickup position while moving the stage;

an image processing unit which compares the detected image signal obtained from the image pickup system with standard reference image signal to detect a defect or defect candidates;

a recording unit which defines image pickup heights for the object in association with the positional information;

a height detection unit for detecting the height of the object at the image pickup position by projecting a slit-shaped light onto a region of said object stretching over an image pickup position picked up by said image pickup means from an angle over 80 degree from normal, dividing an image of said slit-shaped light projected on said position into plural images and detecting said divided plural images with a linear image sensor; and a focus control unit which focuses the image pickup system by using the image pickup heights recorded in the recording unit and the surface height detected at the image pickup position by the height detection unit.

25. A defect detection apparatus according to claim 24 wherein the illumination means uses DUV light to illuminate the object.

26. A defect detection apparatus according to claim 24 wherein the image pickup system is provided with a TDI sensor and a surface image of the object is obtained by detecting an optical surface image of the object with the TDI sensor.

27. A defect detection apparatus according to claim 24 wherein the height detection unit irradiates an illuminating light beam, independent of the illumination means, onto a surface of the object and detects the reflected beam from the object to detect the surface height of the object at the image pickup position.

28. A defect detection apparatus according to claim 24 wherein the control unit controls the height of the stage by using the object height information calculated sequentially by the calculation unit.

* * * * *